US010662485B2

(12) United States Patent
Ecker et al.

(10) Patent No.: US 10,662,485 B2
(45) Date of Patent: May 26, 2020

(54) BIOAGENT DETECTION OLIGONUCLEOTIDES

(71) Applicant: IBIS BIOSCIENCES, INC., Carlsbad, CA (US)

(72) Inventors: David J. Ecker, Encinitas, CA (US); Steven A. Hofstadler, Vista, CA (US); Rangarajan Sampath, San Diego, CA (US); Lawrence B. Blyn, Mission Viejo, CA (US); Thomas A. Hall, Oceanside, CA (US); Mark W. Eshoo, Solana Beach, CA (US)

(73) Assignee: IBIS BIOSCIENCES, INC., Carlsbad, CA (US)

( * ) Notice: Subject to any disclaimer, the term of this patent is extended or adjusted under 35 U.S.C. 154(b) by 0 days.

(21) Appl. No.: 15/952,912

(22) Filed: Apr. 13, 2018

(65) Prior Publication Data

US 2018/0230521 A1 Aug. 16, 2018

Related U.S. Application Data

(62) Division of application No. 14/369,618, filed as application No. PCT/US2012/071830 on Dec. 27, 2012, now Pat. No. 9,970,061.

(60) Provisional application No. 61/580,499, filed on Dec. 27, 2011.

(51) Int. Cl.
| | | |
|---|---|---|
| *C07H 21/04* | (2006.01) |
| *C12Q 1/68* | (2018.01) |
| *C12Q 1/689* | (2018.01) |
| *C12Q 1/6853* | (2018.01) |
| *C12Q 1/686* | (2018.01) |

(52) U.S. Cl.
CPC .......... *C12Q 1/689* (2013.01); *C12Q 1/6853* (2013.01); *C12Q 1/686* (2013.01); *C12Q 2600/158* (2013.01); *C12Q 2600/166* (2013.01)

(58) Field of Classification Search
None
See application file for complete search history.

(56) References Cited

U.S. PATENT DOCUMENTS

| | | |
|---|---|---|
| 4,458,066 A | 7/1984 | Caruthers et al. |
| 4,683,195 A | 7/1987 | Mullis et al. |
| 4,683,202 A | 7/1987 | Mullis |
| 4,800,159 A | 1/1989 | Mullis et al. |
| 4,965,188 A | 10/1990 | Mullis et al. |
| 5,130,238 A | 7/1992 | Malek et al. |
| 5,234,809 A | 8/1993 | Boom et al. |
| 5,270,184 A | 12/1993 | Walker et al. |
| 5,283,174 A | 2/1994 | Arnold, Jr. et al. |
| 5,399,491 A | 3/1995 | Kacian et al. |
| 5,455,166 A | 10/1995 | Walker |
| 5,474,796 A * | 12/1995 | Brennan .............. B01J 19/0046 422/547 |
| 5,480,784 A | 1/1996 | Kacian et al. |
| 5,484,908 A | 1/1996 | Froehler et al. |
| 5,502,177 A | 3/1996 | Matteucci et al. |
| 5,645,985 A | 7/1997 | Froehler et al. |
| 5,710,029 A | 1/1998 | Ryder et al. |
| 5,763,588 A | 6/1998 | Matteucci et al. |
| 5,824,518 A | 10/1998 | Kacian et al. |
| 5,830,653 A | 11/1998 | Froehler et al. |
| 5,925,517 A | 7/1999 | Tyagi et al. |
| 5,928,862 A | 7/1999 | Morrison |
| 6,005,096 A | 12/1999 | Matteucci et al. |
| 6,007,992 A | 12/1999 | Lin et al. |
| 6,028,183 A | 2/2000 | Lin et al. |
| 6,150,097 A | 11/2000 | Tyagi et al. |
| 6,303,305 B1 | 10/2001 | Wittwer et al. |
| 6,534,274 B2 | 3/2003 | Becker et al. |
| 6,541,205 B1 | 4/2003 | Yokoyama et al. |
| 7,108,974 B2 | 9/2006 | Ecker et al. |
| 7,217,510 B2 | 5/2007 | Ecker et al. |
| 7,226,739 B2 | 6/2007 | Ecker et al. |
| 7,255,992 B2 | 8/2007 | Ecker et al. |
| 7,312,036 B2 | 12/2007 | Sampath et al. |
| 7,339,051 B2 | 3/2008 | Crooke et al. |
| 7,449,328 B2 | 11/2008 | Hogan |
| 8,057,993 B2 | 11/2011 | Ecker et al. |
| 2003/0027135 A1 | 2/2003 | Ecker et al. |
| 2003/0167133 A1 | 9/2003 | Ecker et al. |
| 2003/0167134 A1 | 9/2003 | Ecker et al. |
| 2003/0170682 A1 | 9/2003 | Rabbani et al. |
| 2003/0175695 A1 | 9/2003 | Ecker et al. |

(Continued)

FOREIGN PATENT DOCUMENTS

| | | |
|---|---|---|
| EP | 0684315 A1 | 11/1995 |
| WO | WO-02070664 A2 | 9/2002 |

(Continued)

OTHER PUBLICATIONS

NEB catalog (1998/1999), pp. 121, 284. (Year: 1998).*
Thompson "A Synchronous Coefficient of Drag Alteration (SCODA) Based Technique for Sequence Specific Enrichment of Nucleic Acids" BASe, The University of British Columbia, 2002, 1-143.
Jansen et al., "Rapid identification of bacteria in blood cultures by using fluorescently labeled oligonucleotide probes." J Clin Microbiol. Feb. 2000;38(2):814-7.
Beaucage S.L., et al., "Deoxynucleoside Phosphoramidites—A New Class of Key Intermediates For Deoxypolynucleotide Synthesis," Tetrahedron Letters, 1981, vol. 22 (20), pp. 1859-1862.

(Continued)

*Primary Examiner* — Jeanine A Goldberg
(74) *Attorney, Agent, or Firm* — David Casimir; Casimir Jones, S.C.

(57) ABSTRACT

The present invention compositions, methods and systems to identify, detect, and/or quantify bacterial DNA in the presence of contaminating non-bacterial DNA. In particular, the present invention provides oligonucleotides configured to detect a relatively small amount of bacterial DNA in the presence of an overwhelmingly large amount of contaminating human DNA.

17 Claims, 8 Drawing Sheets

Specification includes a Sequence Listing.

(56) References Cited

U.S. PATENT DOCUMENTS

| | | |
|---|---|---|
| 2003/0175696 A1 | 9/2003 | Ecker et al. |
| 2003/0175697 A1 | 9/2003 | Ecker et al. |
| 2003/0187588 A1 | 10/2003 | Ecker et al. |
| 2003/0187593 A1 | 10/2003 | Ecker et al. |
| 2003/0190605 A1 | 10/2003 | Ecker et al. |
| 2003/0225529 A1 | 12/2003 | Ecker et al. |
| 2003/0228571 A1 | 12/2003 | Ecker et al. |
| 2004/0072242 A1* | 4/2004 | Hunter ............... C12Q 1/689 435/7.1 |
| 2004/0110169 A1 | 6/2004 | Ecker et al. |
| 2004/0117129 A1 | 6/2004 | Ecker et al. |
| 2004/0121309 A1 | 6/2004 | Ecker et al. |
| 2004/0121310 A1 | 6/2004 | Ecker et al. |
| 2004/0121311 A1 | 6/2004 | Ecker et al. |
| 2004/0121312 A1 | 6/2004 | Ecker et al. |
| 2004/0121313 A1 | 6/2004 | Ecker et al. |
| 2004/0121314 A1 | 6/2004 | Ecker et al. |
| 2004/0121315 A1 | 6/2004 | Ecker et al. |
| 2004/0121329 A1 | 6/2004 | Ecker et al. |
| 2004/0121335 A1 | 6/2004 | Ecker et al. |
| 2004/0121340 A1 | 6/2004 | Ecker et al. |
| 2004/0122598 A1 | 6/2004 | Ecker et al. |
| 2004/0122857 A1 | 6/2004 | Ecker et al. |
| 2004/0161770 A1 | 8/2004 | Ecker et al. |
| 2004/0185438 A1 | 9/2004 | Ecker |
| 2004/0202997 A1 | 10/2004 | Ecker et al. |
| 2004/0209260 A1 | 10/2004 | Ecker et al. |
| 2004/0219517 A1 | 11/2004 | Ecker et al. |
| 2004/0253583 A1 | 12/2004 | Ecker et al. |
| 2004/0253619 A1 | 12/2004 | Ecker et al. |
| 2005/0027459 A1 | 2/2005 | Ecker et al. |
| 2005/0123952 A1 | 6/2005 | Griffey et al. |
| 2005/0130168 A1 | 6/2005 | Han et al. |
| 2005/0130196 A1 | 6/2005 | Hofstadler et al. |
| 2005/0142581 A1 | 6/2005 | Griffey et al. |
| 2005/0164215 A1 | 7/2005 | Hofstadler et al. |
| 2005/0266397 A1 | 12/2005 | Ecker et al. |
| 2005/0270191 A1 | 12/2005 | Hofstadler et al. |
| 2006/0014154 A1 | 1/2006 | Eshoo |
| 2006/0046246 A1 | 3/2006 | Zeng et al. |
| 2006/0046265 A1 | 3/2006 | Becker et al. |
| 2006/0121520 A1 | 6/2006 | Ecker et al. |
| 2006/0205040 A1 | 9/2006 | Sampath |
| 2006/0240412 A1 | 10/2006 | Hall et al. |
| 2006/0259249 A1 | 11/2006 | Sampath et al. |
| 2006/0275749 A1 | 12/2006 | Sampath et al. |
| 2006/0275788 A1 | 12/2006 | Ecker et al. |
| 2007/0087336 A1 | 4/2007 | Sampath et al. |
| 2007/0087337 A1 | 4/2007 | Sampath et al. |
| 2007/0087338 A1 | 4/2007 | Sampath et al. |
| 2007/0087339 A1 | 4/2007 | Sampath et al. |
| 2007/0087340 A1 | 4/2007 | Sampath et al. |
| 2007/0087341 A1 | 4/2007 | Sampath et al. |
| 2007/0184434 A1 | 8/2007 | Sampath et al. |
| 2007/0218467 A1 | 9/2007 | Ecker et al. |
| 2007/0218489 A1 | 9/2007 | Sampath et al. |
| 2007/0224614 A1 | 9/2007 | Sampath et al. |
| 2007/0238116 A1 | 10/2007 | Sampath et al. |
| 2007/0243544 A1 | 10/2007 | Sampath et al. |
| 2007/0248969 A1 | 10/2007 | Sampath et al. |
| 2008/0138808 A1 | 6/2008 | Hall et al. |
| 2008/0145847 A1 | 6/2008 | Hall et al. |
| 2008/0146455 A1 | 6/2008 | Hall et al. |
| 2008/0160512 A1 | 7/2008 | Ecker et al. |
| 2008/0233570 A1 | 9/2008 | Hall et al. |
| 2008/0311558 A1 | 12/2008 | Ecker et al. |
| 2009/0004643 A1 | 1/2009 | Ecker et al. |
| 2009/0035777 A1 | 2/2009 | Kokoris et al. |
| 2009/0047665 A1 | 2/2009 | Hall et al. |
| 2009/0139867 A1 | 6/2009 | Marziali et al. |
| 2009/0280471 A1* | 11/2009 | Ecker ............... C12Q 1/689 435/5 |
| 2011/0104696 A1 | 5/2011 | Anda et al. |
| 2015/0184231 A1 | 7/2015 | Ecker et al. |
| 2017/0039316 A1* | 2/2017 | Fofanov ............... C12Q 1/689 |

FOREIGN PATENT DOCUMENTS

| | | |
|---|---|---|
| WO | WO-03001976 A2 | 1/2003 |
| WO | WO-03100035 A2 | 12/2003 |
| WO | WO-2004009849 A1 | 1/2004 |
| WO | WO-04052175 A2 | 6/2004 |
| WO | WO-04053076 A2 | 6/2004 |
| WO | WO-04053141 A2 | 6/2004 |
| WO | WO-04053164 A1 | 6/2004 |
| WO | WO-04060278 A2 | 7/2004 |
| WO | WO-04093644 A2 | 11/2004 |
| WO | WO-04101809 A2 | 11/2004 |
| WO | WO-04111187 A2 | 12/2004 |
| WO | WO-05024046 A2 | 3/2005 |
| WO | WO-2005023083 A2 | 3/2005 |
| WO | WO-2005023986 A2 | 3/2005 |
| WO | WO-05036369 A2 | 4/2005 |
| WO | WO-2005033271 A2 | 4/2005 |
| WO | WO-2005072854 A1 | 8/2005 |
| WO | WO-05086634 A2 | 9/2005 |
| WO | WO-05089128 A2 | 9/2005 |
| WO | WO-05091971 A2 | 10/2005 |
| WO | WO-05092059 A2 | 10/2005 |
| WO | WO-05094421 A2 | 10/2005 |
| WO | WO-05098047 A2 | 10/2005 |
| WO | WO-05116263 A2 | 12/2005 |
| WO | WO-05117270 A2 | 12/2005 |
| WO | WO-06019784 A2 | 2/2006 |
| WO | WO-06034294 A1 | 3/2006 |
| WO | WO-06071241 A2 | 7/2006 |
| WO | WO-2006081691 A1 | 8/2006 |
| WO | WO-06094238 A2 | 9/2006 |
| WO | WO-06116127 A2 | 11/2006 |
| WO | WO-06135400 A2 | 12/2006 |
| WO | WO-2007014045 A2 | 2/2007 |
| WO | WO-2007047778 A2 | 4/2007 |
| WO | WO-2007086904 A2 | 8/2007 |
| WO | WO-2007100397 A2 | 9/2007 |
| WO | WO-2007118222 A2 | 10/2007 |
| WO | WO 2012092540 | 7/2012 |

OTHER PUBLICATIONS

Blyn B., et al., "Rapid Detection and Molecular Serotyping of Adenovirus by Use of PCR Followed by Electrospray Ionization Mass Spectrometry," Journal of Clinical Microbiology, 2008, vol. 46 (2), pp. 644-651.

Bowen J.E., et al., "The Native Virulence Plasmid Combination Affects the Segregational Stability of a Thetareplicating Shuttle Vector in Bacillus Anthracis Var," Journal of Applied Microbiology, 1999, vol. 87 (2), pp. 270-278.

Broemeling D.J., et al., "An Instrument for Automated Purification of Nucleic Acids from Contaminated Forensic Samples," Journal of the Association for Laboratory Automation, 2008. vol. 13 (1), pp. 40-48.

Brown E.L., et al., "Chemical Synthesis and Cloning of a Tyrosine tRNA Gene," Methods in Enzymology, 1979, vol. 68, pp. 109-151.

Chen L., et al., "Total Nucleic Acid Analysis integrated on Microfluidic Devices," Lab on a Chip, 2007, vol. 7 (11), pp. 1413-1423.

Crevillen A.G., et al., "Real Sample Analysis on Microfluidic Devices," Talanta, 2007, vol. 74 (3), pp. 342-357.

Ecker D.J., et al., "Ibis T5000: A Universal Biosensor Approach for Microbiology." Nature Reviews Microbiology, 2008, vol. 6 (7), pp. 553-558.

Ecker D.J., et al., "Rapid Identification and Strain-Typing of Respiratory Pathogens for Epidemic Surveillance," Proceedings of the National Academy of Sciences, 2005, vol. 102 (22), pp. 8012-8017.

Ecker J.A., et al., "Identification of Acinetobacter Species and Genotyping of Acinetobacter Baumannii by Multilocus PCR and Mass Spectrometry," Journal of Clinical Microbiology, 2006, vol. 44 (8), pp. 2921-2932.

Eshoo M.W., et al., "Direct Broad-range Detection of Alphaviruses in Mosquito Extracts," Virology, 2007, vol. 368 (2), pp. 286-295.

Franke T.A., et al., "Microfluidics for Miniaturized Laboratories on a Chip," Chemphyschem, 2008, vol. 9 (15), pp. 2140-2156.

(56) References Cited

OTHER PUBLICATIONS

Guatelli J.C., et al., "Isothermal, in Vitro Amplification of Nucleic Acids by a Multienzyme Reaction Modeled after Retroviral Replication," Proceedings of the National Academy of Sciences, 1990, vol. 87 (5), pp. 1874-1878.
Hall T.A., et al., "Base Composition Analysis of Human Mitochondrial DNA Using Electrospray Ionization Mass Spectrometry: A Novel Tool for the Identification and Differentiation of Humans," Analytical Biochemistry, 2005, vol. 344 (1), pp. 53-69.
Hannis J.C., et al., "High-Resolution Genotyping of Campylobacter Species by Use of PCR and High-Throughput Mass Spectrometry," Journal of Clinical Microbiology, 2008, vol. 46 (4), pp. 1220-1225.
Hill F., et al., "Polymerase Recognition of Synthetic Oligodeoxyribonucleotides Incorporating Degenerate Pyrimidine and Purine Bases," Proceedings of the National Academy of Sciences, 1998, vol. 95, pp. 4258-4263.
Hujer K.M., et al., "Analysis of Antibiotic Resistance Genes in Multidrug-resistant Acinetobacter Sp. Isolates from Military and Civilian Patients Treated at the Walter Reed Army Medical Center," Antimicrob Agents Chemother, 2006, vol. 50 (12), pp. 4114-4123.
Hwang K.Y., et al., "Bacterial Dna Sample Preparation from Whole Blood Using Surface-modified Si Pillar Arrays," Analytical Chemistry, 2008, vol. 80 (20), pp. 7786-7791.
International Search Report and Written Opinion for Application No. PCT/US2012/071830, dated Apr. 15, 2013, 13 pages.
Jin L.Q., et al., "Detection and Identification of Intestinal Pathogenic Bacteria by Hybridization to Oligonucleotide Microarrays," World Journal of Gastroenterology, 2005, vol. 11 (48), pp. 7615-7619.
Kwoh D.Y., et al., "Transcription-Based Amplificaton System and Detection of Amplified Human Immunodeficiency Viru: Type 1 with A Bead-Based Sandwixh Hybridization Format," Proceeding of the National Academy of Sciences of the USA, 1989, vol. 86 (4), pp. 1173-1177.
Lizaradi P.M., et al., "Exponential Amplification of Recombinant-RNA Hybridization Probes," Bio/Technology, 1988, vol. 6, pp. 1197-1202.
Loakes D., et al., "Nitroindoles as Universal Bases," Nucleosides and Nucleotides, 1995, vol. 14 (3-5), pp. 1001-1003.
MacLean D., et al., "Application of 'next-generation' Sequencing Technologies to Microbial Genetics," Nature Reviews Microbiology, 2009, vol. 7 (4), pp. 287-296.
Magnuson V.L., et al., "Substrate Nucleotide-Determined Non-Templated Addition of Adenine by Taq DNA Polymerase; Implications for PCR-Based Genotyping and Cloning," Bio Techniques, 1996, vol. 21 (4), pp. 700-709.
Marziali A., et al., "Novel Electrophoresis Mechanism Based on Synchronous Alternating Drag Perturbation," Electrophoresis, 2005, vol. 26 (1), pp. 82-90.
Matteucci M.D., et al., "Synthesis of Deoxyoligonucleotides on a Polymer Support," Journal of the American Chemical Society, 1981, vol. 103 (11), pp. 3185-3191.
Maxam A.M., et al., "A New Method for Sequencing Dna," Proceedings of the National Academy of Sciences of the United States of America, 1977, vol. 74 (2), pp. 560-564.
Mitra R.D., et al., "In Situ Localized Amplification and Contact Replication of Many Individual DNA Molecules," Nucleic Acids Research, 1999, vol. 27 (24), pp. e34.

Morozova O., et al., "Applications of Next-generation Sequencing Technologies in Functional Genomics," Genomics, 2008, vol. 92 (5), pp. 255-264.
Mullis K.B., et al., "Specific Synthesis of Dna In Vitro Via a Polymerase-catalyzed Chain Reaction," Methods in Enzymology, 1987, vol. 155, pp. 335-350.
Murakawa G. J., et al., "Direct detection of HIV-1 RNA from AIDS and ARC patient samples", DNA., 1988, 7 (4), 287-295.
Narang S.A., et al., "Improved Phosphotriester Method for the Synthesis of Gene Fragments," Methods in Enzymology, 1979, vol. 68, pp. 90-98.
Nyren P., "The History of Pyrosequencing," Methods in Molecular Biology, 2007, vol. 373, pp. 1-14.
Ohno K., et al., "Microfluidics: Applications for Analytical Purposes in Chemistry and Biochemistry," Electrophoresis, 2008, vol. 29 (22), pp. 4443-4453.
Ong S.E., et al., "Fundamental Principles and Applications of Microfluidic Systems," Frontiers in Bioscience, 2008, vol. 13, pp. 2757-2773.
Persing, "In Vitro Nucleic Acid Amplification Techniques," Diagnostic Molecular Microbiology, 1993, pp. 51-77.
Ronaghi M., et al., "A sequencing method based on real-time pyrophosphate," Science, 1998, vol. 281 (5375), pp. 363-365.
Ronaghi M., et al., "Real-time Dna Sequencing Using Detection of Pyrophosphate Release," Analytical Biochemistry, 1996, vol. 242 (1), pp. 84-89.
Sala M., et al., "Ambiguous Base Pairing of the Purine Analogue 1-(2-Deoxy-B-D-Ribofuranosyl)-Imidazole-4-Carboxamide During PCR," Nucleic Acids Research, 1996, vol. 24 (17), pp. 3302-3306.
Sampath R., et al., "Global Surveillance of Emerging Influenza Virus Genotypes by Mass Spectrometry," Plos One, 2007, vol. 2 (5), pp. e489.
Sampath R., et al., "Rapid Identification of Emerging Infectious Agents using PCR and Electrospray Ionization Mass Spectrometry," Annals of the New York Academy of Science, 2007, vol. 1102, pp. 109-120.
Sampath R., et al., "Rapid Identification of Emerging Pathogens: Coronavirus," Emerging Infectious Diseases, 2005, vol. 11 (3), pp. 373-379.
Sanger F., et al., "DNA Sequencing with Chain-Terminating Inhibitors," Proceedings of the National Academy of Sciences, 1977, vol. 74 (12), pp. 5463-5467.
Smith L.M., et al., "Fluorescence Detection in Automated Dna Sequence Analysis," Nature, 1986, vol. 321 (6071), pp. 674-679.
Smith T.F., et al., "Comparison of Biosequences," Advances in Applied Mathematics, 1981, vol. 2, pp. 482-489.
Van Aerschot A., et al., "In Search of Acyclic Analogues as Universal Nucleosides in Degenerate Probes," Nucleosides and Nucelotides, 1995, vol. 14 (3-5), pp. 1053-1056.
Voelkerding K.V., et al., "Next-Generation Sequencing: from Basic Research to Diagnostics," Clinical Chemistry, 2009, vol. 55 (4), pp. 641-658.
Walker G.T., et al., "Isothermal in Vitro Amplification of DNA by a Restriction Enzyme/DNA Polymerase System," Proceedings of the National Academy of Sciences, 1992, vol. 89 (1) pp. 392-396.
Weiss R., "Hot Prospect for New Gene Amplifier," Science, 1991, vol. 254 (5036), pp. 1292-1293.
Wortmann G., et al., "Genotypic Evolution of Acinetobacter Baumannii Strains in an Outbreak Associated with War Trauma," Infection Control and Hospital Epidemiology, 2008, vol. 29 (6), pp. 553-555.

\* cited by examiner

BIOAGENT DETECTION OLIGONUCLEOTIDES

CROSS-REFERENCE TO RELATED APPLICATIONS

The present Application is a divisional of U.S. application Ser. No. 14/369,618 filed Jun. 27, 2014, which is a national phase application under 35 U.S.C. § 371 of PCT International Application No. PCT/US2012/071830 filed on Dec. 27, 2012, which claims priority to U.S. Provisional Application Ser. No. 61/580,499 filed Dec. 27, 2011, the entirety of which is incorporated by reference herein.

FIELD OF THE INVENTION

The present invention provides compositions, methods and systems to identify, detect, and/or quantify bacterial DNA in the presence of contaminating non-bacterial DNA. In particular, the present invention provides oligonucleotides configured to detect a relatively small amount of bacterial DNA in the presence of an overwhelmingly large amount of contaminating human DNA.

BACKGROUND OF THE INVENTION

Rapid and definitive microbial identification is desirable for a variety of industrial, medical, environmental, quality, and research reasons. Traditionally, the microbiology laboratory has functioned to identify the etiologic agents of infectious diseases through direct examination and culture of specimens. Since the mid-1980s, researchers have repeatedly demonstrated the practical utility of molecular biology techniques, many of which form the basis of clinical diagnostic assays. Some of these techniques include nucleic acid hybridization analysis, restriction enzyme analysis, genetic sequence analysis, and separation and purification of nucleic acids (See, e.g., J. Sambrook, E. F. Fritsch, and T. Maniatis, Molecular Cloning: A Laboratory Manual, 2nd Ed., Cold Spring Harbor Laboratory Press, Cold Spring Harbor, N.Y., 1989). These procedures, in general, are time-consuming and tedious and require large and complex analytical equipment.

SUMMARY OF THE INVENTION

In some embodiments, the present invention provides a composition comprising a purified oligonucleotide configured to hybridize to a broad range of bacterial genomes while discriminating against hybridizing to non-bacterial DNA. In some embodiments, the oligonucleotide is between 10 and 20 nucleotides in length. In some embodiments, the oligonucleotide hybridizes to over 100 bacterial genomes. In some embodiments, the non-bacterial DNA comprises human genomic DNA.

In some embodiments, the present invention provides a method comprising: (a) providing: (i) one or more purified oligonucleotides configured to hybridize to a broad range of bacterial genomes while discriminating against hybridizing to human genomic DNA; and (ii) a sample comprising human genomic DNA, contaminants, and possibly bacterial DNA; (b) contacting the sample with the oligonucleotides; (c) allowing the oligonucleotides to hybridize to bacterial DNA, if bacterial DNA is present in the sample; and (d) detecting bacterial DNA, if bacterial DNA is present in the sample, based upon hybridization to the oligonucleotides. In some embodiments, the broad range of bacterial genomes comprises over 100 bacterial genomes. In some embodiments, the method further comprises quantifying the bacterial DNA. In some embodiments, the method further comprises using SCODA to separate the bacterial DNA from the human genomic DNA.

In some embodiments, the present invention provides a kit comprising a plurality of purified oligonucleotides configured to hybridize to a broad range of bacterial genomes while discriminating against hybridizing to non-bacterial DNA. In some embodiments, the oligonucleotides are between 10 and 20 nucleotides in length.

In some embodiments, the non-bacterial DNA comprises human genomic DNA. In some embodiments, the kit further comprises a gel suitable for use in SCODA purification. In some embodiments, the kit further comprises a component for generating an electric field.

BRIEF DESCRIPTION OF THE DRAWINGS

The foregoing summary and detailed description is better understood when read in conjunction with the accompanying drawings which are included by way of example and not by way of limitation.

DESCRIPTION OF THE INVENTION

The present invention relates to portable systems and devices, and corresponding methods, for detecting bioagents. In particular, the present invention provides systems, devices, and methods that utilize one or more of a sample preparation component, sample analysis component employing broad range primers, and sample detection component.

In some embodiments, the systems, devices, and methods are embodied in a portable format. The portable systems and devices may be hand-held sized or may be larger. Portability permits the use of the systems and devices outside of traditional laboratory settings. In some embodiments, devices are provided having a length, a width, and depth. In some embodiments, the length, width, and depth are each, independently, less than 0.5 meters (e.g., less than 0.3 meters, less than 0.2 meters, less than 0.1 meters, less than 0.05 meters, less than 0.03 meters, less than 0.02 meters, less than 0.01 meters, or less than 0.005 meters). In some embodiments, the weight of the device is less than 10 kg (e.g., less than 5 kg, less than 3 kg, less than 2 kg, less than 1 kg, less than 0.5 kg, less than 0.3 kg, less than 0.2 kg, or less than 0.1 kg).

In some embodiments, the systems and device combine one or more of sample preparation, sample analysis, and sample detection. For example, in some embodiments, the systems and devices combine sample preparation and single molecule-based analysis and detection of nucleic acid molecules. In some embodiments, the small size of the systems and devices is achieved by minimizing the need to extensively move sample and fluid through large numbers of different compartments. For example, in some embodiments, the systems and devices use three or fewer chambers to process samples: a sample preparation chamber, a sample analysis chamber, and a sample detection chamber. One or more of these functionalities may be combined (i.e., a single chamber provide two or all three of these functions). Chambers are preferably fluidically connected by microchannels. Miniaturization is further enhanced by the use of consumable kit cartridges that provide target-specific and general reagents. An example comprises the uses of electrodynamic fields (e.g., SCODA) for nucleic acid isolation. PCR with broad range primers for nucleic acid amplification and next-generation sequencing approaches for nucleic acid analysis, and detection via electrostatic fields and nanopores.

Figure 5:
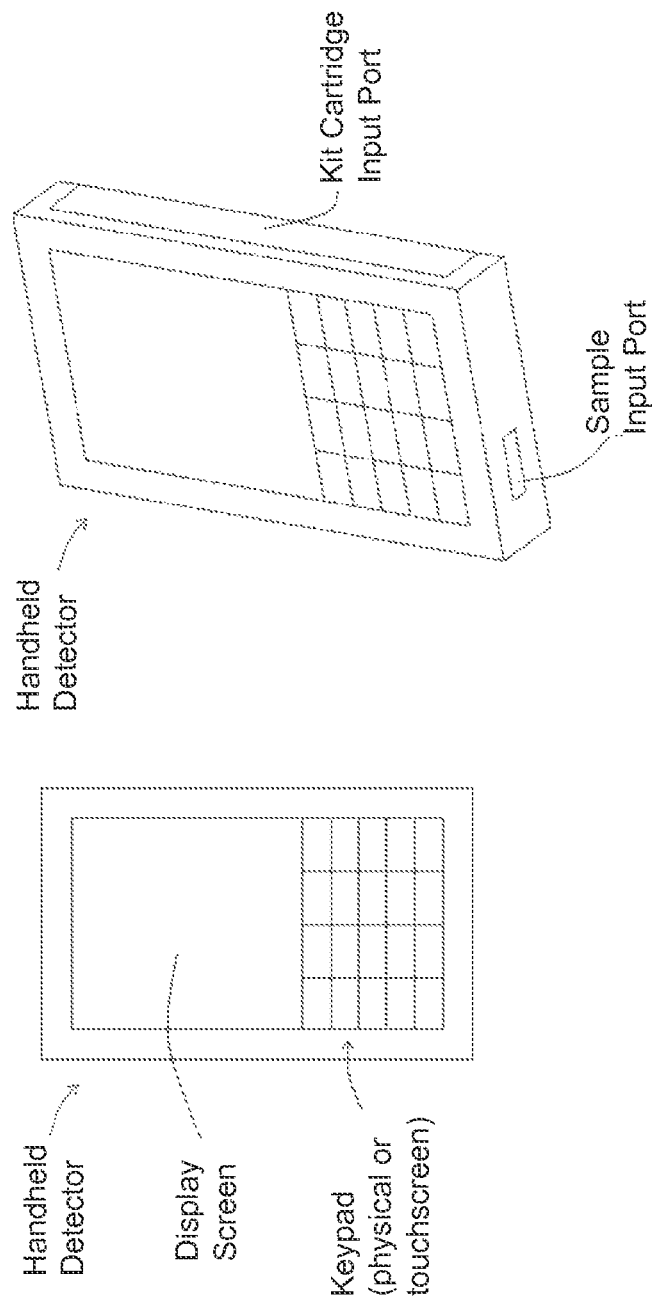
FIG. 5 shows an exemplary handheld device of the invention.
Figure 6:
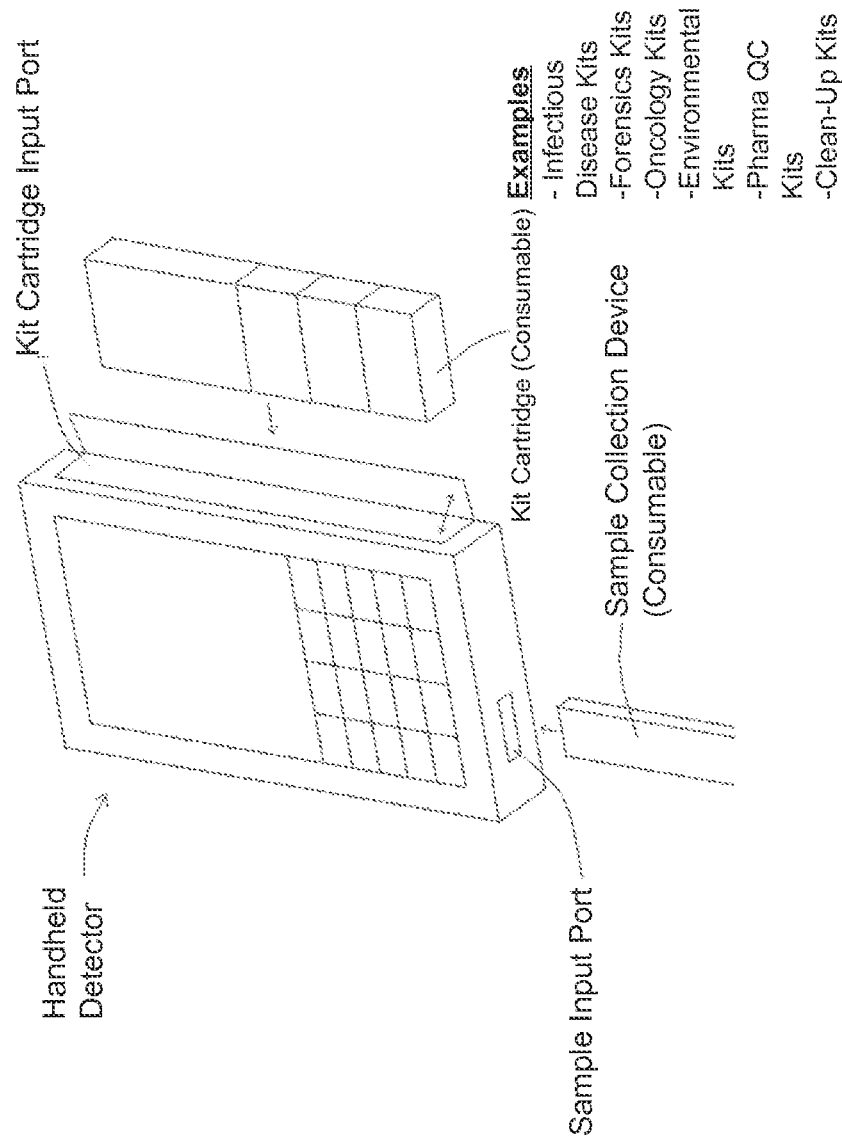
FIG. 6 shows an exemplary handheld device of the invention with consumables.

An exemplary handheld device is shown in FIG. 5. This embodiment provides a user interface that includes a keypad, which can be a physical keypad or a touchscreen, and a display screen. The keypad permits the user to input instructions or data into the device. Such instructions and data include, but are not limited to, sample identification, date, time, user name, selection of sample type, selection of analysis type, selection of sample processing conditions, selection of sample analysis conditions (e.g., number of cycles of an amplification reaction), selection of detection conditions, selection of data display formats, and the like. In some embodiments, the device comprises computer memory that stores data. In some embodiments, the device comprises a sample input port. The sample input port may be configured in any desired manner to accept desired sample types. Exemplary sample input ports permit sample input from syringes, hoses, droppers, pipettes, and the like. In some embodiments, the devices further comprise a kit cartridge input port. Such ports permit addition of single-use or multi-use reagents to the device for carrying out one or more sample preparation, analysis, or detection steps. Cassettes may provide target-specific reagents (e.g., primers for detection of particular pathogens). Thus, in some embodiments, the device is able to detect any desired target analyte through the addition of interchangeable, consumable, target-specific cassettes containing appropriate reagents (e.g., target-specific reagents, general reagents, buffers, positive and negative control reagents, etc.) for the target of interest. FIG. 6 provides an exemplary device showing consumable sample input and reagent cartridges.

In some embodiments, the systems and devices are configured to carry out sample preparation and processing, but not analysis. In some such embodiments, the sample is prepared in a manner that permits its transfer to different analytical equipment for analysis. For example, in some embodiments, the device permits nucleic acid isolation and amplification (e.g., using broad range primers) and the amplified nucleic acid molecules are packaged for transfer to a different analytical device (e.g., a mass spectrometer).

In some embodiments, the systems and devices comprise wireless communication components to permit wireless transfer of data, instructions, or other information. For example, in some embodiments, data collected by the system or device is transmitted to a remote processing location. In some embodiments, the data is compressed prior to transfer. In some embodiments, the transferred data is processed (e.g., compared to a database to identify or otherwise characterize an unknown target nucleic acid molecule) and the processed data is presented to the user. In some embodiments, the data is presented by transfer back to the device and the analysis is displayed on the device. In other embodiments, the data is made available over a public or private electronic communication system (e.g., Internet, phone, etc.).

Figure 7:
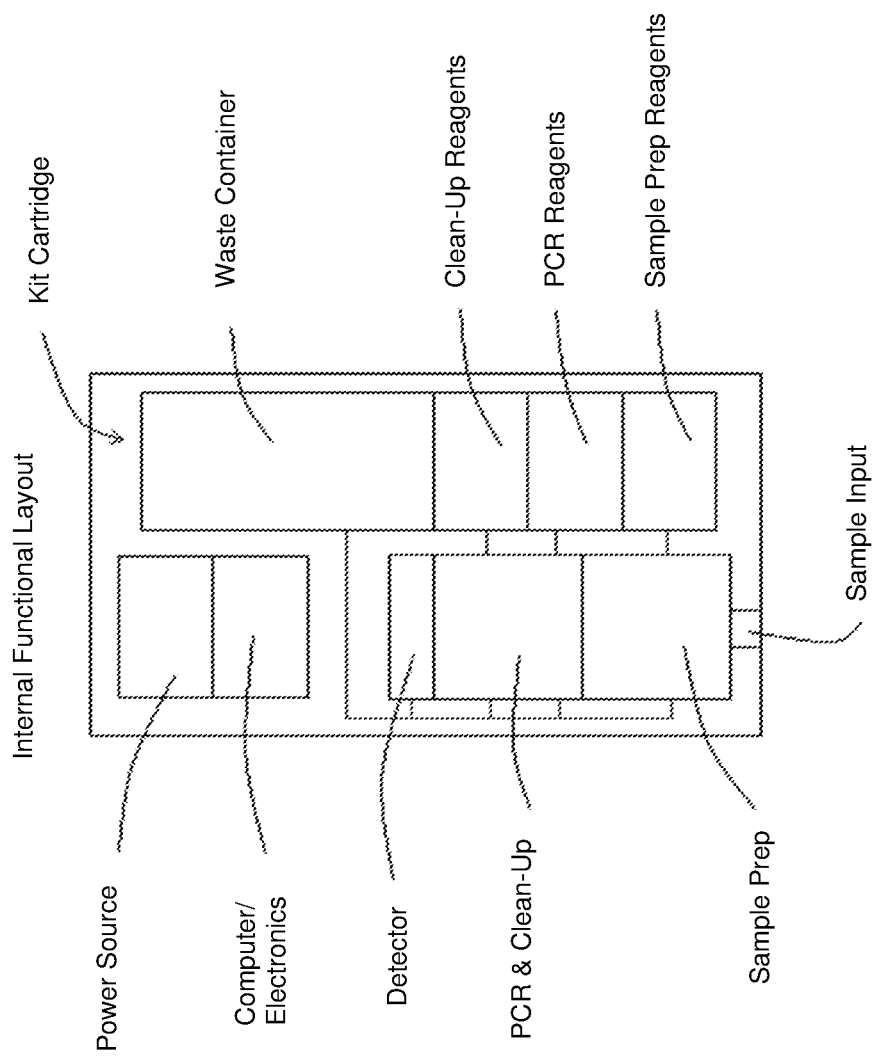
FIG. 7 shows an internal configuration of an exemplary handheld device.

The internal layout of the device is configured with one or more chambers for storing reagents and carrying out the processing steps. An exemplary configuration is shown in FIG. 7. In this embodiment, a first region comprises a power source. In some embodiments, the power source comprises one or more batteries. In some embodiments, the power source is configured for receipt of power from an external power source. A second region provides a computer and other necessary electronics. The computer comprises a processor and computer memory. The device may contain a wired or wireless data transfer component to permit transfer of data to and/or from the computer. A third region provides a sample preparation chamber in communication with the sample input port. The sample preparation chamber is in liquid communication with a sample preparation reagent housing of the kit cartridge that contains reagents for sample preparation. In some embodiments, the sample preparation chamber isolates and purifies nucleic acid molecules from samples. A fourth region, a sample analysis chamber, is in liquid communication with the sample preparation chamber and receives purified nucleic acid molecules from the sample preparation chamber. FIG. 7 exemplifies the analysis chamber as a polymerase chain reaction (PCR) chamber for carrying out nucleic acid amplification and post-amplification clean-up. The analysis chamber is in liquid communication with reagent chambers in the kit cartridge that provide PCR reagents and PCR clean-up reagents. A fifth region, a sample detector region, is in liquid communication with the sample analysis chamber and receives amplified nucleic acid from the analysis chamber. The detector contains optical, fluorescent, luminescent, or other signal detection components to detect the presence of, or identity of, the target nucleic acid molecule. The detection component is in liquid communication with a waste container in the kit cartridge such that all reagents may be removed and disposed with the consumable kit cartridge. In some embodiments, the kit cartridge contains a wash reservoir that provides a wash solution to clean all chambers of the device.

The systems and devices of the present invention may be configured to work with a wide variety of sample types, analysis methods, and detection systems. Non-limiting examples of each are provided below.

Sample Preparation

The present invention is not limited by the nature of the sample that is analyzed. Samples include both biological samples (e.g., blood, sputum, urine, tissue, nasopharyngeal or nasal swabs, nasal wash or aspirate, etc.) and environmental samples (e.g., air, water, etc.).

The sample preparation component of the systems and devices may include microfluidic channels and chambers to permit proper processing of the sample. Exemplary microfluidic systems are described in Ohno et al., Electrophoresis, 29:4443 (2008), Franke and Wixforth, Chemphyschem., 24:2140 (2008), Crevillen et al., Talanta, 74:342 (2007), Ong and Du, Front Biosci., 13:2757 (2008), and Chen and Day, Lab Chip, 7:1413 (2007), herein incorporated by reference in their entireties.

In some embodiments, sample is exposed to appropriate reagents to release (e.g., lyse) nucleic acid from cells, tissues, or other sample types. In some embodiments, capture components or molecules (e.g., beads) are used to isolate the nucleic acid from the non-nucleic acid components of the sample. Any of a wide variety of nucleic acid isolation or capture technologies may be used in the sample preparation component of the systems, devices, and methods.

In some embodiments, cell capture technologies are use to isolate cells or other materials containing a target nucleic acid away from other cells and sample material. For example, in some embodiments, ADEMTECH VIRO ADEMBEADS are used for magnetic separation of viral particles. In other embodiments, Si-pillar arrays are used to capture cells (see e.g., Hwang et al., Anal. Chem., 80:7786 (2008), herein incorporated by reference in its entirety).

Cell lysis can be conducted using chemical (e.g., chaotropic salts, GITC, guanidinium-HCl, urea, phenol, NaOH/KOH, detergents, etc.), temperature (boiling, freeze/thaw, microwave), physical (e.g., pressure, bead beating, French Press, sonication, grinding, mortar/pestle/$SiO_2$), enzymatic (e.g., lysozymes, glycanases, proteases, Proteinase K), or osmosis (e.g., osmotic shock, low salt buffers) approaches, or combinations thereof. Lysis can be organisms-specific or non-organisms-specific.

Nucleic acid isolation from lysed cellular material or other materials can be conducted by Solid Phase Reversible Immobilization using magnetic microparticles (see e.g., U.S. Pat. No. 5,234,809, herein incorporated by reference in its entirety). In some embodiments, capture oligonucleotides complementary to a target nucleic acid of interest are employed.

In some embodiments, sample preparation employs a SCODA method. In certain embodiments, broad range primers (e.g., as disclosed herein) are immobilized in a SCODA gel (e.g., by cross-linking the primers in the gel). In this regard, immobilized primers serve as broad capture oligonucleotides. In general, a sample is loaded into such a SCODA gel, which not only allows total nucleic acid to be purified and concentrated from contaminants, but also allows the target nucleic acid (e.g., a portion of a pathogen genome) to be selectively concentrated from other non-target nucleic acid. In certain embodiments, the selectively concentrated target nucleic acid is eluted from the SCODA gel and subjected to amplification methods in order to detect the target nucleic acid. In particular embodiments, the concentrated nucleic acid is subjected to broad range priming, using, for example, at least some of the same primers immobilized in the SCODA gel. In some embodiments, the same set of immobilized primers is used as primers to amplify the target nucleic acid. In certain embodiments, the SCODA gel immobilized primers are: complementary to the broad range primers described further below that are complementary to variable regions that flank a conserved regions in target pathogens; are complementary to the broad range primers used in the mass spectrometry methods described below (e.g., IBIS TIGER methods); used to capture based on other broadly conserved domains that flank the primers generally employed in the mass spectrometry methods described below; contain "wild-card" inosine bases; or are composed of mixtures of oligonucleotides which take into account known mixtures/heteroplasmies/SNPs in the capture sequences.

In particular embodiments, prior to loading a sample (e.g., a crude sample, such a blood, serum, saliva, air sample, water sample, etc.) onto a SCODA gel, it is subjected to processing with restriction enzymes. In other embodiments, the concentrated nucleic acid eluted from the SCODA gel is subjected to processing by restriction enzymes. Preferably, the restriction enzymes are selected to ensure digestion around the target areas of interest (e.g., regions that have primer binding sites that are variable, but surround a conserved region).

In certain embodiments, the gel immobilized SCODA primers (capture oligonucleotides) are used to perform in situ PCR methods in the SCODA gel in order to amplify the target sequence prior to detection or elution and detection. In certain embodiments, the electrical or other fields used in the SCODA method are used to promote hybridization and disassociation of the target nucleic acid and immobilized primers in order to facilitate rounds of PCR.

In other embodiments, the concentrated target nucleic acid (e.g., bound to the capture oligonucleotides in the gel) are directly detected without eluting from the gel. For example, in certain embodiments, the capture oligonucleotides are detectably labeled such that hybridization with target nucleic acid (if present) can be directly detected.

As indicated above, embodiments of the present invention provide for the use of SCODA methods with broad range primers immobilized in a SCODA gel as capture oligonucleotides. SCODA is a method of particle separation and concentration that may be used to purify highly negatively charged molecules such as nucleic acid (e.g., DNA). SCODA methods, compositions, and devices are described in: U.S. Provisional Application 60/540,352, filed 2 Feb. 2004, U.S. Provisional Application 60/634,604, filed Dec. 10, 2004; Marziali, A.; et al., Electrophoresis, 2005, 26, 82-89; Broemeling et al., JALA Charlottesv Va., 2008 February; 13(1):40-48, WO06/081691, filed Feb. 7, 2006; and WO05/072854, filed Feb. 2, 2005, all of which are herein incorporated by reference in their entireties as if fully set forth herein. SCODA can be used to concentrate the particles in the vicinity of a point in a region of a suitable material in which the particles have mobilities that vary in response to an applied field or combination of applied fields. Where the particles are electrically-charged molecules, such as DNA, the applied fields may comprise electric fields. The material may comprise a suitable gel such as an agarose gel, for example. SCODA does not require electrodes to be present at the location where particles are concentrated. In one embodiment, SCODA provides focusing and concentration of molecules based on the non-linear dependence of the particles' velocity on the strength of an applied electric field. This can also be stated as being based on the field dependence of the particles' mobility.

Particles may be injected into a region of a medium within which the particles can be concentrated by SCODA by providing the particles in an adjacent region and applying a field that causes the particles to move into the region of the SCODA medium. The adjacent region may be called a first region and the region of the SCODA medium may be called a second region. The field that causes the particles to move from the first region into the second region may be called a first field. The first field may comprise any field to which particles of interest respond by moving. Where the particles are electrically charged, the first field may comprise an electric field. Depending upon the nature of the particles of interest, the first field may comprise any of: a magnetic field; an electric field; a flow field; or combination thereof.

Sample Analysis

Purified nucleic acid molecules may be analyzed by a wide variety of methods. In some embodiments, analysis comprises nucleic acid amplification. In some embodiments, no nucleic acid amplification is employed. In some embodiments, nucleic acid sequence is determined. In some embodiments, sequence is not determined. In some embodiments, broad range priming is used in conjunction with amplification, sequencing, or other analysis techniques.

Broad Range Primers

Embodiments of the present employ broad range primers as capture oligonucleotides and/or amplification primers. Broad range primers refer to primers that hybridize to regions of a target nucleic acid that are conserved between two or more organisms or cells or loci and that, when two primers are used, flank a variable region that differs between said two or more organisms or cells or loci. In some embodiments, the two or more organisms differ in their genotype, strain, sub-species, species, genus, family, order, class, phylum, or kingdom. For example, in some embodiments, a first organism is a particular genus of bacteria and the second organism is a different genus of bacteria. In other embodiments, the first and second organisms are the same genus, but different species of bacteria. In other embodiments, the first organism is a bacterium and the second organism is a virus or a mammal. In some embodiments, the broad range primers are used to generate amplicons from target nucleic acid molecules in a sample to facilitate analysis of or determine the presence of the target nucleic acid molecules.

One with ordinary skill in the art of design of primers will recognize that a given primer need not hybridize with 100% complementarity in order to effectively prime the synthesis of a complementary nucleic acid strand. Primer pair sequences may be a "best fit" amongst the aligned bioagent sequences, thus they need not be fully complementary to the hybridization region of any one of the bioagents in the alignment. Moreover, a primer may hybridize over one or more segments such that intervening or adjacent segments are not involved in the hybridization event (e.g., for example, a loop structure or a hairpin structure). The primers may comprise at least 70%, at least 75%, at least 80%, at least 85%, at least 90%, at least 95% or at least 99% sequence identity with a target nucleic acid of interest. Thus, in some embodiments, an extent of variation of 70% to 100%, or any range falling within, of the sequence identity is possible relative to the specific primer sequences disclosed herein. To illustrate, determination of sequence identity is described in the following example: a primer 20 nucleobases in length which is identical to another 20 nucleobase primer having two non-identical residues has 18 of 20 identical residues (18/20=0.9 or 90% sequence identity). In another example, a primer 15 nucleobases in length having all residues identical to a 15 nucleobase segment of primer 20 nucleobases in length would have 15/20=0.75 or 75% sequence identity with the 20 nucleobase primer. Percent identity need not be a whole number, for example when a 28 consecutive nucleobase primer is completely identical to a 31 consecutive nucleobase primer (28/31=0.9032 or 90.3% identical).

Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). In some embodiments, complementarity of primers with respect to the conserved priming regions of viral nucleic acid, is between about 70% and about 80%. In other embodiments, homology, sequence identity or complementarity, is between about 80% and about 90%. In yet other embodiments, homology, sequence identity or complementarity, is at least 90%, at least 92%, at least 94%, at least 95%, at least 96%, at least 97%, at least 98%, at least 99% or is 100%.

In some embodiments, the primers described herein comprise at least 70%, at least 75%, at least 80%, at least 85%, at least 90%, at least 92%, at least 94%, at least 95%, at least 96%, at least 98%, or at least 99%, or 100% (or any range falling within) sequence identity with the primer sequences specifically disclosed herein.

In some embodiments, the oligonucleotide primers are 13 to 35 nucleobases in length (13 to 35 linked nucleotide residues). These embodiments comprise oligonucleotide primers 13, 14, 15, 16, 17, 18, 19, 20, 21, 22, 23, 24, 25, 26, 27, 28, 29, 30, 31, 32, 33, 34 or 35 nucleobases in length, or any range therewithin.

In some embodiments, any given primer comprises a modification comprising the addition of a non-templated T residue to the 5' end of the primer (i.e., the added T residue does not necessarily hybridize to the nucleic acid being amplified). The addition of a non-templated T residue has an effect of minimizing the addition of non-templated A residues as a result of the non-specific enzyme activity of, e.g., Taq DNA polymerase (Magnuson et al., *Biotechniques,* 1996: 21, 700-709), an occurrence which may lead to ambiguous results arising from molecular mass analysis.

Primers may contain one or more universal bases. Because any variation (due to codon wobble in the third position) in the conserved regions among species is likely to occur in the third position of a DNA (or RNA) triplet, oligonucleotide primers can be designed such that the nucleotide corresponding to this position is a base which can bind to more than one nucleotide, referred to herein as a "universal nucleobase." For example, under this "wobble" base pairing, inosine (I) binds to U, C or A; guanine (G) binds to U or C, and uridine (U) binds to U or C. Other examples of universal nucleobases include nitroindoles such as 5-nitroindole or 3-nitropyrrole (Loakes et al., *Nucleosides and Nucleotides,* 1995, 14, 1001-1003), the degenerate nucleotides dP or dK, an acyclic nucleoside analog containing 5-nitroindazole (Van Aerschot et al., *Nucleosides and Nucleotides.,* 1995, 14, 1053-1056) or the purine analog 1-(2-deoxy-beta-D-ribofuranosyl)-imidazole-4-carboxamide (Sala et al., *Nucl. Acids Res.,* 1996, 24, 3302-3306).

In some embodiments, to compensate for weaker binding by the wobble base, oligonucleotide primers are configured such that the first and second positions of each triplet are occupied by nucleotide analogs which bind with greater affinity than the unmodified nucleotide. Examples of these analogs include, but are not limited to, 2,6-diaminopurine which binds to thymine, 5-propynyluracil which binds to adenine and 5-propynylcytosine and phenoxazines, including G-clamp, which binds to G. Propynylated pyrimidines are described in U.S. Pat. Nos. 5,645,985, 5,830,653 and 5,484,908, each of which is commonly owned and incorporated herein by reference in its entirety. Propynylated primers are described in U.S Pre-Grant Publication No. 2003-0170682 also commonly owned and incorporated herein by reference in its entirety. Phenoxazines are described in U.S.

Pat. Nos. 5,502,177, 5,763,588, and 6,005,096, each of which is incorporated herein by reference in its entirety. G-clamps are described in U.S. Pat. Nos. 6,007,992 and 6,028,183, each of which is incorporated herein by reference in its entirety.

In some embodiments, non-template primer tags are used to increase the melting temperature ($T_m$) of a primer-template duplex in order to improve amplification efficiency. A non-template tag is at least three consecutive A or T nucleotide residues on a primer which are not complementary to the template. In any given non-template tag, A can be replaced by C or G and T can also be replaced by C or G. Although Watson-Crick hybridization is not expected to occur for a non-template tag relative to the template, the extra hydrogen bond in a G-C pair relative to an A-T pair confers increased stability of the primer-template duplex and improves amplification efficiency for subsequent cycles of amplification when the primers hybridize to strands synthesized in previous cycles.

In other embodiments, propynylated tags may be used in a manner similar to that of the non-template tag, wherein two or more 5-propynylcytidine or 5-propynyluridine residues replace template matching residues on a primer. In other embodiments, a primer contains a modified internucleoside linkage such as a phosphorothioate linkage, for example.

In some embodiments, the primers contain mass- or mobility-modifying tags. Addition of mass- or mobility-modifying tags to certain nucleobases of a given primer can result in simplification of analysis of a given bioagent identifying amplicon.

In some embodiments, the mass- or mobility-modified nucleobase comprises one or more of the following: for example, 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{13}N$ and $^{13}C$.

Figure 1:
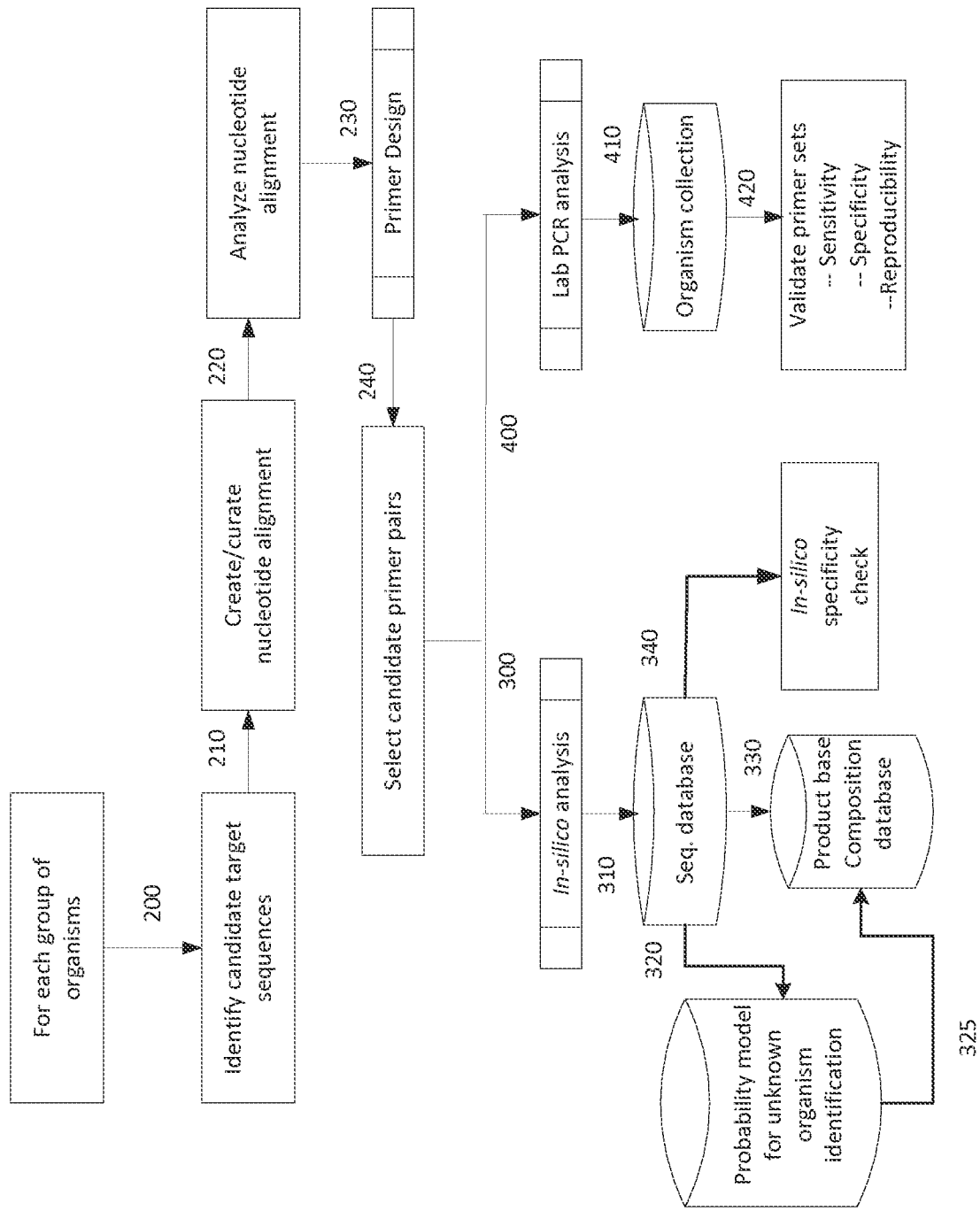
FIG. 1 shows a process diagram illustrating one embodiment of the primer pair selection process.
Figure 2:
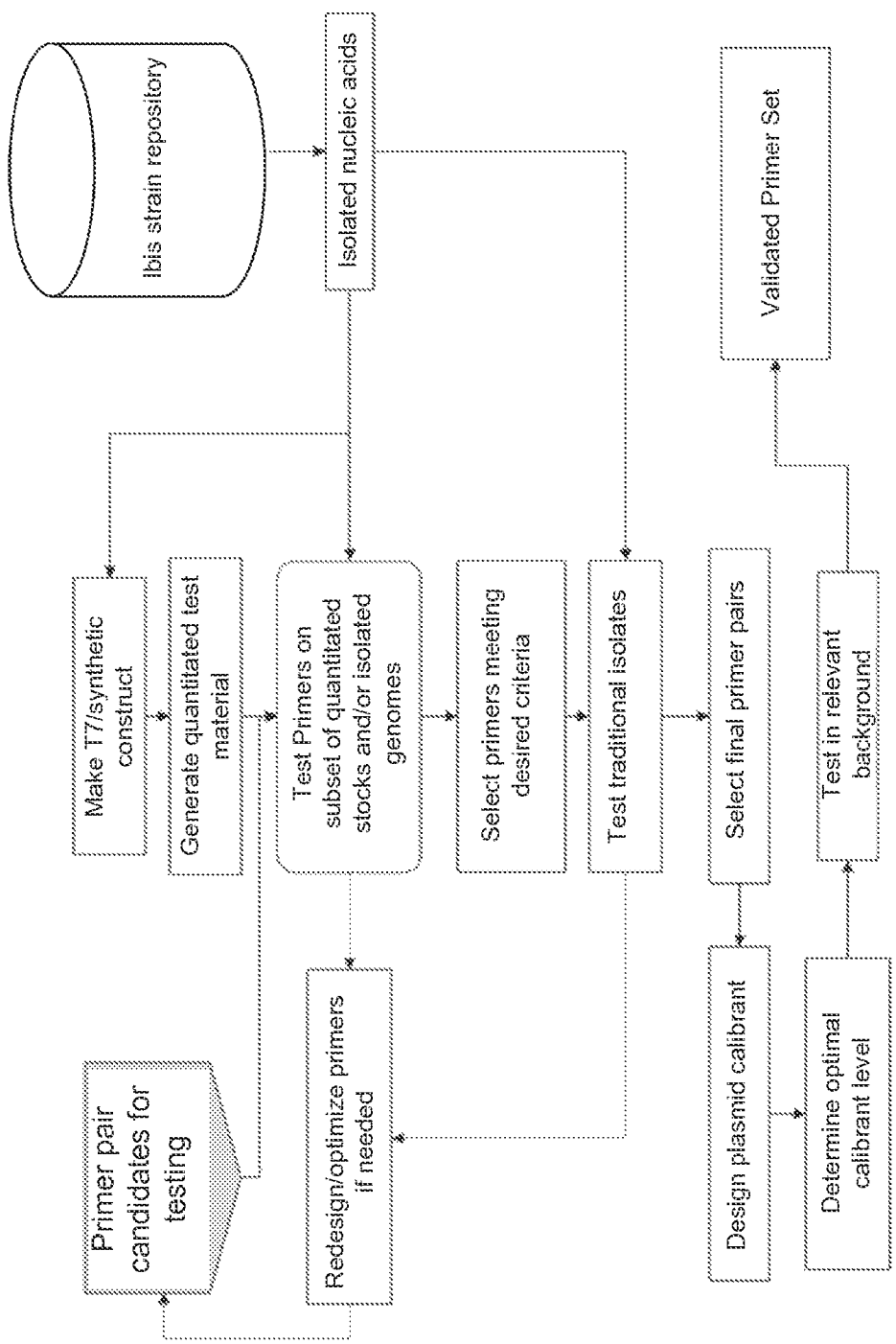
FIG. 2 shows a process diagram illustrating one embodiment of the primer pair validation process. Here, select primers are shown meeting test criteria. Criteria include but are not limited to, the ability to amplify targeted organism nucleic acid, the ability to exclude non-target bioagents, the ability to not produce unexpected amplicons, the ability to not dimerize, the ability to have analytical limits of detection of ≤100 genomic copies/reaction, and the ability to differentiate amongst different target organisms.

One embodiment of a process flow diagram used for primer selection and validation process is depicted in FIGS. 1 and 2. For each group of organisms, candidate target sequences are identified (200) from which nucleotide sequence alignments are created (210) and analyzed (220). Primers are then configured by selecting priming regions (230) to facilitate the selection of candidate primer pairs (240). The primer pair sequence is typically a "best fit" amongst the aligned sequences, such that the primer pair sequence may or may not be fully complementary to the hybridization region on any one of the bioagents in the alignment. Thus, best fit primer pair sequences are those with sufficient complementarity with two or more bioagents to hybridize with the two or more bioagents and generate an amplicon or hybridization complex. Where amplification is desired, the primer pairs are then subjected to in silico analysis by electronic PCR (ePCR) (300) wherein bioagent identifying amplicons are obtained from sequence databases such as GenBank or other sequence collections (310) and tested for specificity in silico (320). Bioagent identifying amplicons obtained from ePCR of GenBank sequences (310) may also be analyzed by a probability model which predicts the capability of a given amplicon to identify unknown bioagents. Where base composition analysis is used, the base compositions of amplicons with favorable probability scores are then stored in a base composition database (325). Alternatively, base compositions of the bioagent identifying amplicons obtained from the primers and GenBank sequences are directly entered into the base composition database (330). Candidate primer pairs (240) are validated by in vitro amplification by a method such as PCR analysis (400) of nucleic acid from a collection of organisms (410). Amplicons thus obtained are analyzed to confirm the sensitivity, specificity and reproducibility of the primers used to obtain the amplicons (420).

Synthesis of primers is well known and routine in the art. The primers may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed.

In some embodiments, a bioagent identifying amplicon or hybridization complex may be produced using only a single primer (either the forward or reverse primer of any given primer pair), provided an appropriate amplification method is chosen, such as, for example, low stringency single primer PCR (LSSP-PCR).

Examples of broad range primers, and methods of generating and selecting broad range primers are described in U.S. Pat. Nos. 7,108,974; 7,217,510; 7,226,739; 7,255.992; 7,312,036; 7,339,051; patent publication numbers 2003/0027135; 2003/0167133; 2003/0167134; 2003/0175695; 2003/0175696; 2003/0175697; 2003/0187588; 2003/0187593; 2003/0190605; 2003/0225529; 2003/0228571; 2004/0110169; 2004/0117129; 2004/0121309; 2004/0121310; 2004/0121311; 2004/0121312; 2004/0121313; 2004/0121314; 2004/0121315; 2004/0121329; 2004/0121335; 2004/0121340; 2004/0122598; 2004/0122857; 2004/0161770; 2004/0185438; 2004/0202997; 2004/0209260; 2004/0219517; 2004/0253583; 2004/0253619; 2005/0027459; 2005/0123952; 2005/0130196 2005/0142581; 2005/0164215; 2005/0266397; 2005/0270191; 2006/0014154; 2006/0121520; 2006/0205040; 2006/0240412; 2006/0259249; 2006/0275749; 2006/0275788; 2007/0087336; 2007/0087337; 2007/0087338 2007/0087339; 2007/0087340; 2007/0087341; 2007/0184434; 2007/0218467; 2007/0218467; 2007/0218489; 2007/0224614; 2007/0238116; 2007/0243544; 2007/0248969; 2008/0138808; 20080145847; 20080146455; 20080160512; 20080233570; 20080311558; 20090004643; 20090047665; WO2002/070664; WO2003/001976; WO2003/100035; WO2004/009849; WO2004/052175; WO2004/053076; WO2004/053141; WO2004/053164; WO2004/060278; WO2004/093644; WO 2004/101809; WO2004/111187; WO2005/023083; WO2005/023986; WO2005/024046; WO2005/033271; WO2005/036369; WO2005/086634; WO2005/089128; WO2005/091971; WO2005/092059; WO2005/094421; WO2005/098047; WO2005/16263; WO2005/117270; WO2006/019784; WO2006/034294; WO2006/071241; WO2006/094238; WO2006/116127; WO2006/135400; WO2007/014045; WO2007/047778; WO2007/086904; WO2007/100397; WO2007/118222; Ecker et al., Ibis T5000: a universal biosensor approach for microbiology. *Nat Rev Microbiol.* 2008 Jun. 3; Ecker et al., Identification of *Acinetobacter* species and genotyping of *Acinetobacter baumannii* by multilocus PCR and mass spectrometry. *J Clin Microbiol.* 2006 August; 44(8):2921-32.; Ecker et al., Rapid identification and strain-typing of respiratory pathogens for epidemic surveillance. *Proc Natl Acad Sci USA.* 2005 May 31; 102(22):8012-7. Epub 2005 May 23.; Wortmann et al., Genotypic Evolution of *Acinetobacter baumannii* Strains in an Outbreak Associated With War Trauma. *Infect Control Hosp Epidemiol.* 2008 June; 29(6):553-555.; Hannis et al., High-resolution genotyping of *Campylobacter* species by use of PCR and high-throughput mass spectrometry. *J Clin Microbiol.* 2008 April; 46(4): 1220-5.; Blyn et al., Rapid detection and molecular serotyping of adenovirus by use of PCR followed by electrospray ionization mass spectrometry. *J. Clin Microbiol.* 2008 February; 46(2):644-51.; Eshoo et al., Direct broad-range detection of alphaviruses in mosquito extracts. *Virology.* 2007 Nov. 25; 368(2):286-95.; Sampath et al., Global surveillance of emerging Influenza virus genotypes by mass spectrometry. *PLoS ONE.* 2007 May 30; 2(5):e489.; Sampath et al., Rapid identification of emerging infectious agents using PCR and electrospray ionization mass spectrometry. *Ann N Y Acad Sci.* 2007 April; 1102:109-20.; Hujer et al., Analysis of antibiotic resistance genes in multidrug-resistant *Acinetobacter* sp. isolates from military and civilian patients treated at the Walter Reed Army Medical Center. *Antimicrob Agents Chemother.* 2006 December; 50(12): 4114-23.; Hall et al., Base composition analysis of human mitochondrial DNA using electrospray ionization mass spectrometry: a novel tool for the identification and differentiation of humans. *Anal Biochem.* 2005 Sep. 1; 344(1): 53-69.; Sampath et al., Rapid identification of emerging pathogens: coronavirus. *Emerg InJfct Dis.* 2005 March; 11(3):373-9; each of which is herein incorporated by reference in its entirety.

In some embodiments, nucleic acid molecules are analyzed and characterized by any of a wide variety of methods, including, but not limited to, sequencing, hybridization analysis, amplification (e.g., via polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA)).

Nucleic acid may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

The polymerase chain reaction (U.S. Pat. Nos. 4,683,195, 4,683,202, 4,800,159 and 4,965,188, each of which is herein incorporated by reference in its entirety), commonly referred to as PCR, uses multiple cycles of denaturation, annealing of primer pairs to opposite strands, and primer extension to exponentially increase copy numbers of a target nucleic acid sequence. In a variation called RT-PCR, reverse transcriptase (RT) is used to make a complementary DNA (cDNA) from mRNA, and the cDNA is then amplified by PCR to produce multiple copies of DNA. For other various permutations of PCR see, e.g., U.S. Pat. Nos. 4,683,195, 4,683,202 and 4,800,159; Mullis et al., Meth. Enzymol. 155: 335 (1987); and, Murakawa et al., DNA 7: 287 (1988), each of which is herein incorporated by reference in its entirety.

Transcription mediated amplification (U.S. Pat. Nos. 5,480,784 and 5,399,491, each of which is herein incorporated by reference in its entirety), commonly referred to as TMA, synthesizes multiple copies of a target nucleic acid sequence autocatalytically under conditions of substantially constant temperature, ionic strength, and pH in which multiple RNA copies of the target sequence autocatalytically generate additional copies. See, e.g., U.S. Pat. Nos. 5,399, 491 and 5,824,518, each of which is herein incorporated by reference in its entirety. In a variation described in U.S. Publ. No. 20060046265, herein incorporated by reference in its entirety, TMA optionally incorporates the use of blocking moieties, terminating moieties, and other modifying moieties to improve TMA process sensitivity and accuracy.

The ligase chain reaction (Weiss, R., Science 254: 1292 (1991), herein incorporated by reference in its entirety), commonly referred to as LCR, uses two sets of complementary DNA oligonucleotides that hybridize to adjacent regions of the target nucleic acid. The DNA oligonucleotides are covalently linked by a DNA ligase in repeated cycles of thermal denaturation, hybridization and ligation to produce a detectable double-stranded ligated oligonucleotide product.

Strand displacement amplification (Walker, G. et al., Proc. Natl. Acad. Sci. USA 89: 392-396 (1992); U.S. Pat. Nos. 5,270,184 and 5,455,166, each of which is herein incorporated by reference in its entirety), commonly referred to as SDA, uses cycles of annealing pairs of primer sequences to opposite strands of a target sequence, primer extension in the presence of a dNTPaS to produce a duplex hemiphosphorothioated primer extension product, endonuclease-mediated nicking of a hemimodified restriction endonuclease recognition site, and polymerase-mediated primer extension from the 3' end of the nick to displace an existing strand and produce a strand for the next round of primer annealing, nicking and strand displacement, resulting in geometric amplification of product. Thermophilic SDA (tSDA) uses thermophilic endonucleases and polymerases at higher temperatures in essentially the same method (EP Pat. No. 0684315, herein incorporated by reference in its entirety).

Other amplification methods include, for example: nucleic acid sequence based amplification (U.S. Pat. No. 5,130,238, herein incorporated by reference in its entirety), commonly referred to as NASBA; one that uses an RNA replicase to amplify the probe molecule itself (Lizardi et al., BioTechnol. 6: 1197 (1988), herein incorporated by reference in its entirety), commonly referred to as QP-replicase; a transcription based amplification method (Kwoh et al., Proc. Natl. Acad. Sci. USA 86:1173 (1989)); and, self-sustained sequence replication (Guatelli et al., Proc. Natl. Acad. Sci. USA 87: 1874 (1990), each of which is herein incorporated by reference in its entirety). For further discussion of known amplification methods see Persing, David H., "In Vitro Nucleic Acid Amplification Techniques" in Diagnostic Medical Microbiology: Principles and Applications (Persing et al., Eds.), pp. 51-87 (American Society for Microbiology, Washington, D.C. (1993)).

In some embodiments, the molecular mass of a given bioagent identifying amplicon is determined by mass spectrometry. Mass spectrometry is intrinsically a parallel detection scheme without the need for radioactive or fluorescent labels, because an amplicon is identified by its molecular mass. The current state of the art in mass spectrometry is such that less than femtomole quantities of material can be analyzed to provide information about the molecular contents of the sample. An accurate assessment of the molecular mass of the material can be quickly obtained, irrespective of whether the molecular weight of the sample is several hundred, or in excess of one hundred thousand atomic mass units (amu) or Daltons.

In some embodiments, the present invention provides DNA or gene sequencing methodologies and/or technologies. In some embodiments, sequencing methodologies and technologies provided by the present invention comprise traditional or first generation sequencing technologies (Maxam & Gilbert, 1977, Proc Natl Acad Sci USA 74: 560-564; Sanger et al., 1977, Proc Natl Acad Sci USA 74: 5463-5467; herein incorporated by reference in their entireties) which utilize electrophoretic detection on a gel or through capillary electrophoresis ((Smith et al., 1986, Nature 321: 674-679; herein incorporated by reference in its entirety). In some embodiments, DNA sequencing methodologies provided by the present invention comprise Second Generation (a.k.a. Next Generation or Next-Gen), Third Generation (a.k.a. Next-Next-Gen), or Fourth Generation (a.k.a. $N_3$-Gen) sequencing technologies including but not limited to pyrosequencing, sequencing-by-ligation, single molecule sequencing, sequence-by-synthesis (SBS), massive parallel clonal, massive parallel single molecule SBS, massive parallel single molecule real-time, massive parallel single molecule real-time nanopore technology, etc. Morozova and Marra provide a review of some such technologies, Genomics, 92:255 (2008), herein incorporated by reference in its entirety.

In some embodiments, the present invention provides DNA sequencing by pyrosequencing (Ronaghi et al. 1998, Science 281:363, 365; Ronaghi et al. 1996, Analytical Biochemistry 242: 84; Nyrén 2007, Methods Mol Biology 373: 1-14; herein incorporated by reference in their entireties). Pyrosequencing is a method of DNA sequencing based on the "sequencing by synthesis" principle, which relies on detection of pyrophosphate release. "Sequencing by synthesis" involves immobilizing a single strand of the DNA, and synthesizing its complementary strand enzymatically. The pyrosequencing method is based on detecting the activity of DNA polymerase with a chemiluminescent enzyme. Pyrosequencing allows sequencing of a single strand of DNA by synthesizing the complementary strand along it, one base pair at a time, and detecting which base added at each step. The template DNA is immobilized, and solutions of A, C, G, and T nucleotides are added and removed after the reaction, sequentially. Chemiluminescence is produced when the nucleotide solution complements the next unpaired base of the template. The sequence of solutions which produce chemiluminescent signals provides sequence of the template.

In some embodiments, the present invention provides DNA sequencing by 454 sequencing by ROCHE LIFE SCIENCES. 454 sequencing by ROCHE LIFE SCIENCES provides SBS pyrosequencing which can be performed in Polony beads deposited in 44 pun picoliter wells, provides very long read lengths (400-500 bases), and can yield approximately 400-600 Mbases/run or 1 billion bases/day. 454 sequencing finds utility in de novo sequencing, resequencing, expression tags, transcriptome sequencing, ChIP, methylation analysis, etc. 454 sequencing involves annealing of ssDNA to an excess of DNA capture beads, emulsification of beads and PCR reagents in water-in-oil microreactors, clonal amplification, breaking of microreactors, and enrichment for DNA positive beads. 454 sequencing is performed on a GENOME FLX SEQUENCER.

In some embodiments, the present invention provides DNA sequencing by SOLID sequencing by APPLIED BIOSYSTEMS. SOLID sequencing by APPLIED BIOSYSTEMS utilizes Polony-based sequencing methodologies (Mitra & Church 1999 Nucleic Acids Res, 27:e34; herein incorporated by reference in its entirety). Polony sequencing provides a nonelectrophoretic sequencing method without in vivo cloning artifacts at a low cost per base. In some embodiments, an in vitro paired-tag library is constructed from genomic DNA. Library molecules are clonally amplified on microbeads by emulsion PCR, the clonal amplification yields polymerase colonies, or polonies, that can be sequenced. Short reads are generated in parallel from the microbeads via a cyclic DNA sequencing strategy that utilizes T4 DNA ligase to selectively tag each microbead with fluorescent labels that correlate with the unique nucleotide sequence present on any given bead. SOLID sequencing provides sequencing by ligation using T4 DNA ligase, fluorescent-labeled degenerate nonamers, "Two Base Encoding" which provides increased accuracy (>99.94%), read length up to 35 bases, and high throughput of 20 Gb/run. SOLID sequencing finds utility in de novo sequencing, targeted and whole genome resequencing, gene expression, transcriptome and methylation analysis. SOLID sequencing is performed on a SOLID 3 platform.

In some embodiments, the present invention provides DNA sequencing by ILLUMINA sequencing technology. ILLUMINA sequencing technology utilizes massively parallel SBS using reverse terminator chemistry. SBS is performed at 4 bases/cycle versus 1 base/cycle for pyrosequencing. ILLUMINA sequencing relies on the attachment of randomly fragmented genomic DNA to a planar, optically transparent surface. Attached DNA fragments are extended and bridge amplified to create an ultra-high density sequencing flow cell with 80-100 million clusters, each containing ~1,000 copies of the same template. These templates are sequenced using a four-color DNA SBS technology that employs reversible terminators with removable fluorescent dyes. In some embodiments, high-sensitivity fluorescence detection is achieved using laser excitation and total internal reflection optics. ILLUMINA sequencing provides read lengths of up to 75 bases, throughput of approximately 10-15 Gb/run, and a paired end strategy allows sequencing from both ends. ILLUMINA sequencing finds utility in de novo sequencing, resequencing, transcriptome analysis, epigenomic/methylation status. ILLUMINA sequencing is performed on a GENOME ANALYZER platform.

In some embodiments, the present invention provides DNA sequencing by TRUE SINGLE MOLECULE SEQUENCING (TSMS) by HELICOS BIOSCIENCES. TSMS provides massive parallel single molecule SBS using 1 base per cycle of pyrosequencing. TSMS does not require any up-front library synthesis steps or PCR amplification, therefore eliminating PCR errors. TSMS relies on attachment of billions of single molecules of sample DNA on an application-specific proprietary surface. The captured strands serve as templates for the sequencing-by-synthesis process in which polymerase and one fluorescently labeled nucleotide (C, G, A or T) are added, polymerase catalyzes the sequence-specific incorporation of fluorescent nucleotides into nascent complementary strands on all the templates, free nucleotides are removed by washing, incorporated nucleotides are imaged and positions recorded, the fluorescent group is removed in a highly efficient cleavage process leaving behind the incorporated nucleotide, and the process continues through each of the other three bases. Multiple four-base cycles result in complementary strands greater than 25 bases in length synthesized on billions of templates, providing a greater than 25-base read from each individual template. TSMS provides very high density arrays (1 million/mm²), low cost/base, two laser system (Cy3 and Cy5-labeled dNTP), and read lengths of read length—20-55 bases. TSMS find utility in human genome resequencing, de novo sequencing. TSMS is performed on the HELISCOPE platform.

In some embodiments, the present invention provides DNA sequencing by VISIGEN BIOTECHNOLOGIES. VISIGEN BIOTECHNOLOGIES sequencing provides massive parallel single molecule sequencing in real-time through engineered DNA polymerases and nucleoside triphosphates which function as direct molecular sensors of DNA base identity. Genetically engineered polymerase is fixed on the surface during synthesis. Fluorescence resonance energy transfer (FRET) is detected between the immobilized polymerase and labeled dNTP as they are incorporated. VISIGEN sequencing provides no up-front amplification or cloning steps, read lengths of 1,000 bases, massive parallel arrays (1 Mb/sec/instrument), and no sequential reagent addition during synthesis. VISIGEN sequencing finds utility in de novo sequencing, resequencing, personalized medicine, clinical diagnostics, forensics, basic research, etc.

In some embodiments, the present invention provides single molecule real time (SMRT) sequencing by PACIFIC BIOSCIENCES. SMRT provides massive parallel single molecule sequencing in real-time. Thousands of zero-mode waveguides (ZMWs) in zeptoliter wells are contained on an array. A single DNA polymerase molecule is attached to the bottom of each waveguide. DNA is synthesized using γ-phosphate group labeled with base-specific fluorophores. Upon incorporation of a phospholinked nucleotide, the DNA polymerase cleaves the dye molecule from the nucleotide when it cleaves the phosphate chain. Fluorophores are detected upon incorporation of the corresponding base by the immobilized polymerase. SMRT provides low reaction volumes, very low fluorescence background, fast cycle times, with long read lengths (approx. 1,000 bases), and no sequential reagent addition during synthesis. SMRT find utility in de novo sequencing, resequencing, etc.

In some embodiments, the Xpandomer technology of STRATOS is used (see e.g., U.S. Pat. Publn. No. 20090035777, herein incorporated by reference in its entirety). In this approach, methods for sequencing a target nucleic acid comprise providing a daughter strand produced by a template-directed synthesis, the daughter strand comprising a plurality of subunits coupled in a sequence corresponding to a contiguous nucleotide sequence of all or a portion of the target nucleic acid, wherein the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand, the Xpandomer comprising the tethers and reporter elements for parsing genetic information in a sequence corresponding to the contiguous nucleotide sequence of all or a portion of the target nucleic acid. Reporter elements of the Xpandomer are then detected.

Sample Detection

Detectors are typically structured to detect detectable signals produced, e.g., in or proximal to another component of the given assay system (e.g., in a container and/or on a solid support). Suitable signal detectors that are optionally utilized, or adapted for use, herein detect, e.g., fluorescence, phosphorescence, radioactivity, absorbance, refractive index, luminescence, or mass. Detectors optionally monitor one or a plurality of signals from upstream and/or downstream of the performance of, e.g., a given assay step. For example, detectors optionally monitor a plurality of optical signals, which correspond in position to "real-time" results. Example detectors or sensors include photomultiplier tubes, CCD arrays, optical sensors, temperature sensors, pressure sensors, pH sensors, conductivity sensors, or scanning detectors. Detectors are also described in, e.g., Skoog et al., Principles of Instrumental Analysis, 5$^{th}$ Ed., Harcourt Brace College Publishers (1998), Currell, Analytical Instrumentation: Performance Characteristics and Quality, John Wiley & Sons, Inc. (2000), Sharma et al., Introduction to Fluorescence Spectroscopy, John Wiley & Sons, Inc. (1999), Valeur, Molecular Fluorescence: Principles and Applications, John Wiley & Sons, Inc. (2002), and Gore, Spectrophotometry and Spectrofluorimetry: A Practical Approach, 2.sup.nd Ed., Oxford University Press (2000), which are each incorporated by reference.

Non-amplified or amplified nucleic acids can be detected by any conventional means. For example, in some embodiments, nucleic acids are detected by hybridization with a detectably labeled probe and measurement of the resulting hybrids. Illustrative non-limiting examples of detection methods are described below.

One illustrative detection method, the Hybridization Protection Assay (HPA) involves hybridizing a chemiluminescent oligonucleotide probe (e.g., an acridinium ester-labeled (AE) probe) to the target sequence, selectively hydrolyzing the chemiluminescent label present on unhybridized probe, and measuring the chemiluminescence produced from the remaining probe in a luminometer. See, e.g., U.S. Pat. No. 5,283,174 and Norman C. Nelson et al., Nonisotopic Probing, Blotting, and Sequencing, ch. 17 (Larry J. Kricka ed., 2d ed. 1995, each of which is herein incorporated by reference in its entirety).

Another illustrative detection method provides for quantitative evaluation of the amplification process in real-time. Evaluation of an amplification process in "real-time" involves determining the amount of amplicon in the reaction mixture either continuously or periodically during the amplification reaction, and using the determined values to calculate the amount of target sequence initially present in the sample. A variety of methods for determining the amount of initial target sequence present in a sample based on real-time amplification are well known in the art. These include methods disclosed in U.S. Pat. Nos. 6,303,305 and 6,541, 205, each of which is herein incorporated by reference in its entirety. Another method for determining the quantity of target sequence initially present in a sample, but which is not based on a real-time amplification, is disclosed in U.S. Pat. No. 5,710,029, herein incorporated by reference in its entirety.

Amplification products may be detected in real-time through the use of various self-hybridizing probes, most of which have a stem-loop structure. Such self-hybridizing probes are labeled so that they emit differently detectable signals, depending on whether the probes are in a self-hybridized state or an altered state through hybridization to a target sequence. By way of non-limiting example, "molecular torches" are a type of self-hybridizing probe that includes distinct regions of self-complementarity (referred to as "the target binding domain" and "the target closing domain") which are connected by a joining region (e.g., non-nucleotide linker) and which hybridize to each other under predetermined hybridization assay conditions. In a preferred embodiment, molecular torches contain single-stranded base regions in the target binding domain that are from 1 to about 20 bases in length and are accessible for hybridization to a target sequence present in an amplification reaction under strand displacement conditions. Under strand displacement conditions, hybridization of the two complementary regions, which may be fully or partially complementary, of the molecular torch is favored, except in the presence of the target sequence, which will bind to the single-stranded region present in the target binding domain and displace all or a portion of the target closing domain. The target binding domain and the target closing domain of a molecular torch include a detectable label or a pair of interacting labels (e.g., luminescent/quencher) positioned so that a different signal is produced when the molecular torch is self-hybridized than when the molecular torch is hybridized to the target sequence, thereby permitting detection of probe:target duplexes in a test sample in the presence of unhybridized molecular torches. Molecular torches and a variety of types of interacting label pairs are disclosed in U.S. Pat. No. 6,534,274, herein incorporated by reference in its entirety.

Another example of a detection probe having self-complementarity is a "molecular beacon." Molecular beacons include nucleic acid molecules having a target complementary sequence, an affinity pair (or nucleic acid arms) holding the probe in a closed conformation in the absence of a target sequence present in an amplification reaction, and a label pair that interacts when the probe is in a closed conformation. Hybridization of the target sequence and the target complementary sequence separates the members of the affinity pair, thereby shifting the probe to an open conformation. The shift to the open conformation is detectable due to reduced interaction of the label pair, which may be, for example, a fluorophore and a quencher (e.g., DAB-CYL and EDANS). Molecular beacons are disclosed in U.S. Pat. Nos. 5,925,517 and 6,150,097, herein incorporated by reference in its entirety.

Other self-hybridizing probes are well known to those of ordinary skill in the art. By way of non-limiting example, probe binding pairs having interacting labels, such as those disclosed in U.S. Pat. No. 5,928,862 (herein incorporated by reference in its entirety) might be adapted for use in the present invention.

In some embodiments, intact molecular ions are generated from amplicons using one of a variety of ionization techniques to convert the sample to the gas phase. These ionization methods include, but are not limited to, electrospray ionization (ESI), matrix-assisted laser desorption ionization (MALDI) and fast atom bombardment (FAB). Upon ionization, several peaks are observed from one sample due to the formation of ions with different charges. Averaging the multiple readings of molecular mass obtained from a single mass spectrum affords an estimate of molecular mass of the bioagent identifying amplicon. Electrospray ionization mass spectrometry (ESI-MS) is particularly useful for very high molecular weight polymers such as proteins and nucleic acids having molecular weights greater than 10 kDa, since it yields a distribution of multiply-charged molecules of the sample without causing a significant amount of fragmentation.

The mass detectors used include, but are not limited to, Fourier transform ion cyclotron resonance mass spectrometry (FT-ICR-MS), time of flight (TOF), ion trap, quadrupole, magnetic sector, Q-TOF, and triple quadrupole.

In some embodiments, assignment of previously unobserved base compositions (also known as "true unknown base compositions") to a given phylogeny can be accomplished via the use of pattern classifier model algorithms. Base compositions, like sequences, may vary slightly from strain to strain within species, for example. In some embodiments, the pattern classifier model is the mutational probability model. In other embodiments, the pattern classifier is the polytope model. A polytope model is the mutational probability model that incorporates both the restrictions among strains and position dependence of a given nucleobase within a triplet. In certain embodiments, a polytope pattern classifier is used to classify a test or unknown organism according to its amplicon base composition.

In some embodiments, it is possible to manage this diversity by building "base composition probability clouds" around the composition constraints for each species. A "pseudo four-dimensional plot" may be used to visualize the concept of base composition probability clouds. Optimal primer design typically involves an optimal choice of bioagent identifying amplicons and maximizes the separation between the base composition signatures of individual bioagents. Areas where clouds overlap generally indicate regions that may result in a misclassification, a problem which is overcome by a triangulation identification process using bioagent identifying amplicons not affected by overlap of base composition probability clouds.

In some embodiments, base composition probability clouds provide the means for screening potential primer pairs in order to avoid potential misclassifications of base compositions. In other embodiments, base composition probability clouds provide the means for predicting the identity of an unknown bioagent whose assigned base composition has not been previously observed and/or indexed in a bioagent identifying amplicon base composition database due to evolutionary transitions in its nucleic acid sequence. Thus, in contrast to probe-based techniques, mass spectrometry determination of base composition does not require prior knowledge of the composition or sequence in order to make the measurement.

Provided herein is bioagent classifying information at a level sufficient to identify a given bioagent. Furthermore, the process of determining a previously unknown base composition for a given bioagent (for example, in a case where sequence information is unavailable) has utility by providing additional bioagent indexing information with which to populate base composition databases. The process of future bioagent identification is thus improved as additional base composition signature indexes become available in base composition databases.

Figure 3:
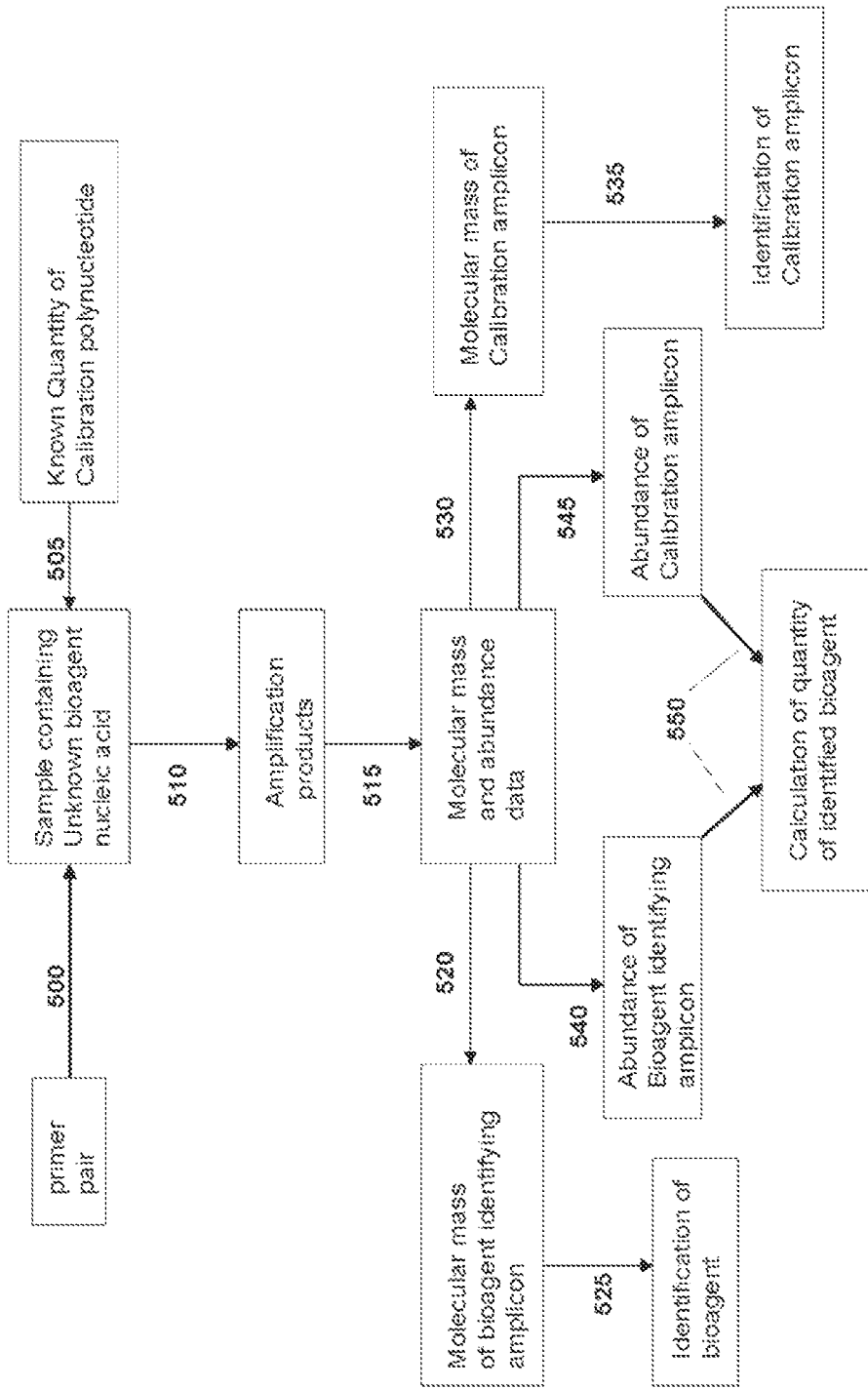
FIG. 3 shows a process diagram illustrating an embodiment of the calibration method.

In some embodiments, the identity and quantity of an unknown bioagent may be determined using the process illustrated in FIG. 3. Primers (500) and a known quantity of a calibration polynucleotide (505) are added to a sample containing nucleic acid of an unknown bioagent. The total nucleic acid in the sample is then subjected to an amplification reaction (510) to obtain amplicons. The molecular masses of amplicons are determined (515) from which are obtained molecular mass and abundance data. The molecular mass of the bioagent identifying amplicon (520) provides for its identification (525) and the molecular mass of the calibration amplicon obtained from the calibration polynucleotide (530) provides for its quantification (535). The abundance data of the bioagent identifying amplicon is recorded (540) and the abundance data for the calibration data is recorded (545), both of which are used in a calculation (550) which determines the quantity of unknown bioagent in the sample.

In certain embodiments, a sample comprising an unknown bioagent is contacted with a primer pair which amplifies the nucleic acid from the bioagent, and a known quantity of a polynucleotide that comprises a calibration sequence. The amplification reaction then produces two amplicons: a bioagent identifying amplicon and a calibration amplicon. The bioagent identifying amplicon and the calibration amplicon are distinguishable by molecular mass while being amplified at essentially the same rate. Effecting differential molecular masses can be accomplished by choosing as a calibration sequence, a representative bioagent identifying amplicon (from a specific species of bioagent) and performing, for example, a 2-8 nucleobase deletion or insertion within the variable region between the two priming sites. The amplified sample containing the bioagent identifying amplicon and the calibration amplicon is then subjected to molecular mass analysis by mass spectrometry, for example. The resulting molecular mass analysis of the nucleic acid of the bioagent and of the calibration sequence provides molecular mass data and abundance data for the nucleic acid of the bioagent and of the calibration sequence. The molecular mass data obtained for the nucleic acid of the bioagent enables identification of the unknown bioagent by base composition analysis. The abundance data enables calculation of the quantity of the bioagent, based on the knowledge of the quantity of calibration polynucleotide contacted with the sample.

In some embodiments, construction of a standard curve in which the amount of calibration or calibrant polynucleotide spiked into the sample is varied provides additional resolution and improved confidence for the determination of the quantity of bioagent in the sample. Alternatively, the calibration polynucleotide can be amplified in its own reaction vessel or vessels under the same conditions as the bioagent. A standard curve may be prepared there from, and the relative abundance of the bioagent determined by methods such as linear regression. In some embodiments, multiplex amplification is performed where multiple bioagent identifying amplicons are amplified with multiple primer pairs which also amplify the corresponding standard calibration sequences. In this or other embodiments, the standard calibration sequences are optionally included within a single construct (preferably a vector) which functions as the calibration polynucleotide.

In some embodiments, the calibrant polynucleotide is used as an internal positive control to confirm that amplification conditions and subsequent analysis steps are successful in producing a measurable amplicon. Even in the absence of copies of the genome of a bioagent, the calibration polynucleotide gives rise to a calibration amplicon. Failure to produce a measurable calibration amplicon indicates a failure of amplification or subsequent analysis step such as amplicon purification or molecular mass determination. Reaching a conclusion that such failures have occurred is, in itself, a useful event. In some embodiments, the calibration sequence is comprised of DNA. In some embodiments, the calibration sequence is comprised of RNA.

In some embodiments, a calibration sequence is inserted into a vector which then functions as the calibration polynucleotide. In some embodiments, more than one calibration sequence is inserted into the vector that functions as the calibration polynucleotide. Such a calibration polynucleotide is herein termed a "combination calibration polynucleotide." It should be recognized that the calibration method should not be limited to the embodiments described herein. The calibration method can be applied for determination of the quantity of any bioagent identifying amplicon when an appropriate standard calibrant polynucleotide sequence is designed and used.

As mentioned above, the systems of the invention also typically include controllers that are operably connected to one or more components (e.g., detectors, databases, thermal modulators, fluid transfer components, robotic material handling devices, and the like) of the given system to control operation of the components. More specifically, controllers are generally included either as separate or integral system components that are utilized, e.g., to receive data from detectors (e.g., molecular masses, etc.), to effect and/or regulate temperature in the containers, or to effect and/or regulate fluid flow to or from selected containers. Controllers and/or other system components are optionally coupled to an appropriately programmed processor, computer, digital device, information appliance, or other logic device (e.g., including an analog to digital or digital to analog converter as needed), which functions to instruct the operation of these instruments in accordance with preprogrammed or user input instructions, receive data and information from these instruments, and interpret, manipulate and report this information to the user. Suitable controllers are generally known in the art and are available from various commercial sources.

Any controller or computer optionally includes a monitor, which is often a cathode ray tube ("CRT") display, a flat panel display (e.g., active matrix liquid crystal display or liquid crystal display), or others. Computer circuitry is often placed in a box, which includes numerous integrated circuit chips, such as a microprocessor, memory, interface circuits, and others. The box also optionally includes a hard disk drive, a floppy disk drive, a high capacity removable drive such as a writeable CD-ROM, and other common peripheral elements. Inputting devices such as a keyboard or mouse optionally provide for input from a user. These components are illustrated further below.

The computer typically includes appropriate software for receiving user instructions, either in the form of user input into a set of parameter fields, e.g., in a graphic user interface (GUI), or in the form of preprogrammed instructions, e.g., preprogrammed for a variety of different specific operations. The software then converts these instructions to appropriate language for instructing the operation of one or more controllers to carry out the desired operation. The computer then receives the data from, e.g., sensors/detectors included within the system, and interprets the data, either provides it in a user understood format, or uses that data to initiate further controller instructions, in accordance with the programming.

Figure 4:
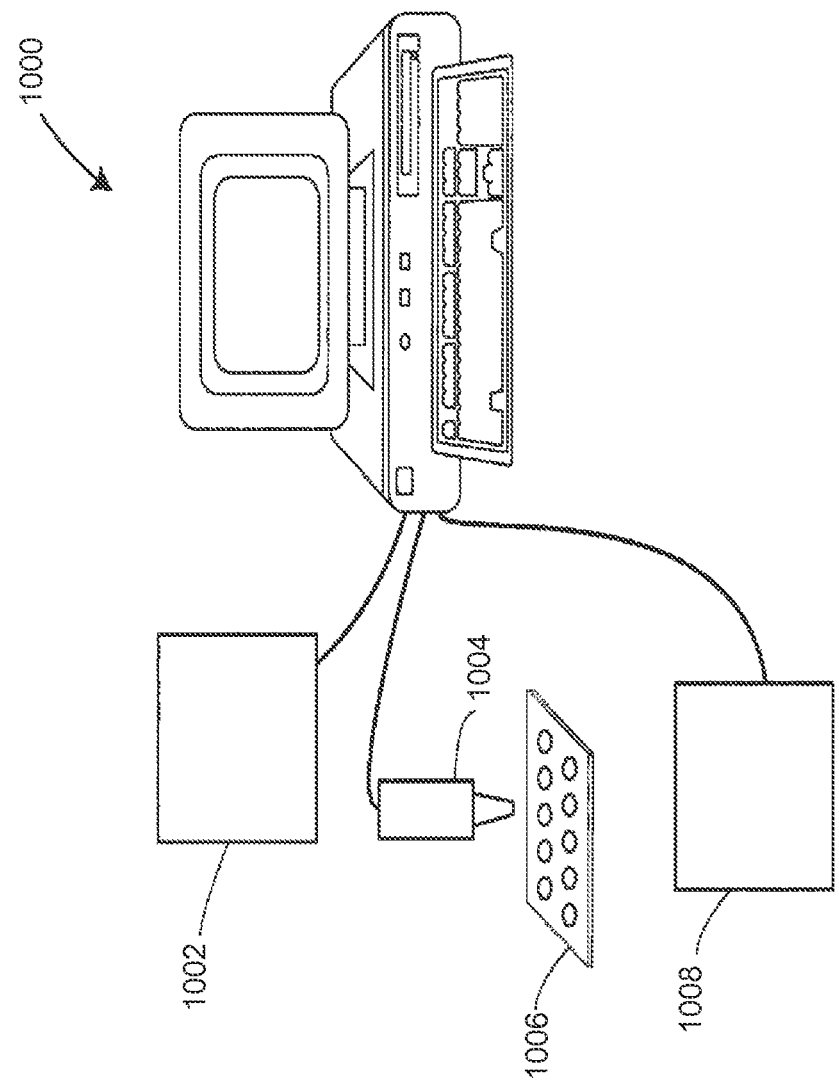
FIG. 4 shows a block diagram showing a representative system.

FIG. 4 is a schematic showing a representative system that includes a logic device in which various aspects of the present invention may be embodied. As will be understood by practitioners in the art from the teachings provided herein, aspects of the invention are optionally implemented in hardware and/or software. In some embodiments, different aspects of the invention are implemented in either client-side logic or server-side logic. As will be understood in the art, the invention or components thereof may be embodied in a media program component (e.g., a fixed media component) containing logic instructions and/or data that, when loaded into an appropriately configured computing device, cause that device to perform as desired. As will also be understood in the art, a fixed media containing logic instructions may be delivered to a viewer on a fixed media for physically loading into a viewer's computer or a fixed media containing logic instructions may reside on a remote server that a viewer accesses through a communication medium in order to download a program component.

More specifically, FIG. 4 schematically illustrates computer 1000 to which mass spectrometer 1002 (e.g., an ESI-TOF mass spectrometer, etc.), fluid transfer component 1004 (e.g., an automated mass spectrometer sample injection needle or the like), and database 1008 are operably connected. Optionally, one or more of these components are operably connected to computer 1000 via a server (not shown in FIG. 4). During operation, fluid transfer component 1004 typically transfers reaction mixtures or components thereof (e.g., aliquots comprising amplicons) from multi-well container 1006 to mass spectrometer 1002. Mass spectrometer 1002 then detects molecular masses of the amplicons. Computer 1000 then typically receives this molecular mass data, calculates base compositions from this data, and compares it with entries in database 1008 to identify the nucleic acid in a given sample. It will be apparent to one of skill in the art that one or more components of the system schematically depicted in FIG. 4 are optionally fabricated integral with one another (e.g., in the same housing).

Definitions

It is to be understood that the terminology used herein is for the purpose of describing particular embodiments only, and is not intended to be limiting. Further, unless defined otherwise, all technical and scientific terms used herein have the same meaning as commonly understood by one of ordinary skill in the art to which this invention pertains. In describing and claiming the present invention, the following terminology and grammatical variants will be used in accordance with the definitions set forth below.

As used herein, the term "about" means encompassing plus or minus 10%. For example, about 200 nucleotides refers to a range encompassing between 180 and 220 nucleotides.

As used herein, the term "amplicon" or "bioagent identifying amplicon" refers to a nucleic acid generated using the primer pairs described herein. The amplicon is typically double stranded DNA; however, it may be RNA and/or DNA:RNA. In some embodiments, the amplicon comprises DNA complementary to target RNA, DNA, or cDNA. In some embodiments, the amplicon comprises sequences of conserved regions/primer pairs and intervening variable region. As discussed herein, primer pairs are configured to generate amplicons from target nucleic acid. As such, the identity or base composition of any given amplicon may include the primer pair, the complement of the primer pair, the conserved regions and the variable region from the bioagent that was amplified to generate the amplicon. One skilled in the art understands that the incorporation of the designed primer pair sequences into an amplicon may replace the native sequences at the primer binding site, and complement thereof. In certain embodiments, after amplification of the target region using the primers the resultant amplicons having the primer sequences are used to generate signal that detects, identifies, or otherwise analyzes the nucleic acid from the tested sample.

Amplicons typically comprise from about 45 to about 200 consecutive nucleobases (i.e., from about 45 to about 200 linked nucleosides), although a wide variety of lengths may be used depending on the detection and analysis methods desired. One of ordinary skill in the art will appreciate that this range expressly embodies compounds of 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, and 200 nucleobases in length. One of ordinary skill in the art will further appreciate that the above range is not an absolute limit to the length of an amplicon, but instead represents a preferred length range.

The term "amplifying" or "amplification" in the context of nucleic acids refers to the production of multiple copies of a polynucleotide, or a portion of the polynucleotide, typically starting from a small amount of the polynucleotide (e.g., a single polynucleotide molecule), where the amplification products or amplicons are generally detectable. Amplification of polynucleotides encompasses a variety of chemical and enzymatic processes. The generation of multiple DNA copies from one or a few copies of a target or template DNA molecule during a polymerase chain reaction (PCR) or a ligase chain reaction (LCR) are forms of amplification. Amplification is not limited to the strict duplication of the starting molecule. For example, the generation of multiple cDNA molecules from a limited amount of RNA in a sample using reverse transcription (RT)-PCR is a form of amplification. Furthermore, the generation of multiple RNA molecules from a single DNA molecule during the process of transcription is also a form of amplification.

As used herein, "bacterial nucleic acid" includes, but is not limited to, DNA, RNA, or DNA that has been obtained from bacterial RNA, such as, for example, by performing a reverse transcription reaction. Bacterial RNA can either be single-stranded (of positive or negative polarity) or double-stranded.

As used herein, the term "base composition" refers to the number of each residue comprised in an amplicon or other nucleic acid, without consideration for the linear arrangement of these residues in the strand(s) of the amplicon. The amplicon residues comprise, adenosine (A), guanosine (G), cytidine, (C), (deoxy)thymidine (T), uracil (U), inosine (I), nitroindoles such as 5-nitroindole or 3-nitropyrrole, dP or dK (Hill F et al., Polymerase recognition of synthetic oligodeoxyribonucleotides incorporating degenerate pyrimidine and purine bases. *Proc Natl Acad Sci USA.* 1998 Apr. 14; 95(8):4258-63), an acyclic nucleoside analog containing 5-nitroindazole (Van Aerschot et al., Nucleosides and Nucleotides, 1995, 14, 1053-1056), the purine analog 1-(2-deoxy-beta-D-ribofuranosyl)-imidazole-4-carboxamide, 2,6-diaminopurine, 5-propynyluracil, 5-propynylcytosine, phenoxazines, including G-clamp, 5-propynyl deoxy-cytidine, deoxy-thymidine nucleotides, 5-propynylcytidine, 5-propynyluridine and mass tag modified versions thereof, including 7-deaza-2'-deoxyadenosine-5-triphosphate, 5-iodo-2'-deoxyuridine-5'-triphosphate, 5-bromo-2'-deoxyuridine-5'-triphosphate, 5-bromo-2'-deoxycytidine-5'-triphosphate, 5-iodo-2'-deoxycytidine-5'-triphosphate, 5-hydroxy-2'-deoxyuridine-5'-triphosphate, 4-thiothymidine-5'-triphosphate, 5-aza-2'-deoxyuridine-5'-triphosphate, 5-fluoro-2'-deoxyuridine-5'-triphosphate, O6-methyl-2'-deoxyguanosine-5'-triphosphate, N2-methyl-2'-deoxyguanosine-5'-triphosphate, 8-oxo-2'-deoxyguanosine-5'-triphosphate or thiothymidine-5'-triphosphate. In some embodiments, the mass-modified nucleobase comprises $^{15}N$ or $^{13}C$ or both $^{15}N$ and $^{13}C$. In some embodiments, the non-natural nucleosides used herein include 5-propynyluracil, 5-propynylcytosine and inosine. Herein the base composition for an unmodified DNA amplicon is notated as $A_w G_x C_y T_z$, wherein w, x, y and z are each independently a whole number representing the number of said nucleoside residues in an amplicon. Base compositions for amplicons comprising modified nucleosides are similarly notated to indicate the number of said natural and modified nucleosides in an amplicon. Base compositions are calculated from a molecular mass measurement of an amplicon, as described below. The calculated base composition for any given amplicon is then compared to a database of base compositions. A match between the calculated base composition and a single database entry reveals the identity of the bioagent.

As used herein, a "base composition probability cloud" is a representation of the diversity in base composition resulting from a variation in sequence that occurs among different isolates of a given species, family or genus. Base composition calculations for a plurality of amplicons are mapped on a pseudo four-dimensional plot. Related members in a family, genus or species typically cluster within this plot, forming a base composition probability cloud.

As used herein, the term "base composition signature" refers to the base composition generated by any one particular amplicon.

As used herein, a "bioagent" means any biological organism or component thereof or a sample containing a biological organism or component thereof, including microorganisms or infectious substances, or any naturally occurring, bioengineered or synthesized component of any such microorganism or infectious substance or any nucleic acid derived from any such microorganism or infectious substance. Those of ordinary skill in the art will understand fully what is meant by the term bioagent given the instant disclosure. Still, a non-exhaustive list of bioagents includes: cells, cell lines, human clinical samples, mammalian blood samples, cell cultures, bacterial cells, viruses, viroids, fungi, protists, parasites, rickettsiae, protozoa, animals, mammals or humans. Samples may be alive, non-replicating or dead or in a vegetative state (for example, vegetative bacteria or spores).

As used herein, a "bioagent division" is defined as group of bioagents above the species level and includes but is not limited to, orders, families, genus, classes, clades, genera or other such groupings of bioagents above the species level.

As used herein, "broad range survey primers" are primers designed to identify an unknown bioagent as a member of a particular biological division (e.g., an order, family, class, clade, or genus). However, in some cases the broad range survey primers are also able to identify unknown bioagents at the species or sub-species level. As used herein, "division-wide primers" are primers designed to identify a bioagent at the species level and "drill-down" primers are primers designed to identify a bioagent at the sub-species level. As used herein, the "sub-species" level of identification includes, but is not limited to, strains, subtypes, variants, and isolates. Drill-down primers are not always required for identification at the sub-species level because broad range survey intelligent primers may, in some cases provide sufficient identification resolution to accomplishing this identification objective.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon hybridization of nucleic acids.

The term "conserved region" in the context of nucleic acids refers to a nucleobase sequence (e.g., a subsequence of a nucleic acid, etc.) that is the same or similar in two or more different regions or segments of a given nucleic acid molecule (e.g., an intramolecular conserved region), or that is the same or similar in two or more different nucleic acid molecules (e.g., an intermolecular conserved region). To illustrate, a conserved region may be present in two or more different taxonomic ranks (e.g., two or more different genera, two or more different species, two or more different subspecies, and the like) or in two or more different nucleic acid molecules from the same organism. To further illustrate, in certain embodiments, nucleic acids comprising at least one conserved region typically have between about 70%-100%, between about 80-100%, between about 90-100%, between about 95-100%, or between about 99-100% sequence identity in that conserved region. A conserved region may also be selected or identified functionally as a region that permits generation of amplicons via primer extension through hybridization of a completely or partially complementary primer to the conserved region for each of the target sequences to which conserved region is conserved.

The term "correlates" refers to establishing a relationship between two or more things. In certain embodiments, for example, detected molecular masses of one or more amplicons indicate the presence or identity of a given bioagent in a sample.

In some embodiments, base compositions are calculated or otherwise determined from the detected molecular masses of amplicons, which base compositions indicate the presence or identity of a given bioagent in a sample.

As used herein, in some embodiments the term "database" is used to refer to a collection of base composition molecular mass data. In other embodiments the term "database" is used to refer to a collection of base composition data. The base composition data in the database is indexed to bioagents and to primer pairs. The base composition data reported in the database comprises the number of each nucleoside in an amplicon that would be generated for each bioagent using each primer. The database can be populated by empirical data. In this aspect of populating the database, a bioagent is selected and a primer pair is used to generate an amplicon. The amplicon's molecular mass is determined using a mass spectrometer and the base composition calculated therefrom without sequencing i.e., without determining the linear sequence of nucleobases comprising the amplicon. Note that base composition entries in the database may be derived from sequencing data (i.e., known sequence information), but the base composition of the amplicon to be identified is determined without sequencing the amplicon. An entry in the database is made to associate correlate the base composition with the bioagent and the primer pair used. The database may also be populated using other databases comprising bioagent information. For example, using the GenBank database it is possible to perform electronic PCR using an electronic representation of a primer pair. This in silico method may provide the base composition for any or all selected bioagent(s) stored in the GenBank database. The information may then be used to populate the base composition database as described above. A base composition database can be in silico, a written table, a reference book, a spreadsheet or any form generally amenable to databases. Preferably, it is in silico on computer readable media.

The term "detect", "detecting" or "detection" refers to an act of determining the existence or presence of one or more targets (e.g., bioagent nucleic acids, amplicons, etc.) in a sample.

As used herein, the term "etiology" refers to the causes or origins, of diseases or abnormal physiological conditions.

As used herein, the term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length sequence or fragment thereof are retained. As used herein, the term "heterologous gene" refers to a gene that is not in its natural environment. For example, a heterologous gene includes a gene from one species introduced into another species. A heterologous gene also includes a gene native to an organism that has been altered in some way (e.g., mutated, added in multiple copies, linked to non-native regulatory sequences, etc). Heterologous genes are distinguished from endogenous genes in that the heterologous gene sequences are typically joined to nucleic acid sequences that are not found naturally associated with the gene sequences in the chromosome or are associated with portions of the chromosome not found in nature (e.g., genes expressed in loci where the gene is not normally expressed).

The terms "homology," "homologous" and "sequence identity" refer to a degree of identity. There may be partial homology or complete homology. A partially homologous sequence is one that is less than 100% identical to another sequence. Determination of sequence identity is described in the following example: a primer 20 nucleobases in length which is otherwise identical to another 20 nucleobase primer but having two non-identical residues has 18 of 20 identical residues (18/20=0.9 or 90% sequence identity). In another example, a primer 15 nucleobases in length having all residues identical to a 15 nucleobase segment of a primer 20 nucleobases in length would have 15/20=0.75 or 75% sequence identity with the 20 nucleobase primer. In context of the present invention, sequence identity is meant to be properly determined when the query sequence and the subject sequence are both described and aligned in the 5' to 3' direction. Sequence alignment algorithms such as BLAST, will return results in two different alignment orientations. In the Plus/Plus orientation, both the query sequence and the subject sequence are aligned in the 5' to 3' direction. On the other hand, in the Plus/Minus orientation, the query sequence is in the 5' to 3' direction while the subject sequence is in the 3' to 5' direction. It should be understood that with respect to the primers of the present invention, sequence identity is properly determined when the alignment is designated as Plus/Plus. Sequence identity may also encompass alternate or "modified" nucleobases that perform in a functionally similar manner to the regular nucleobases adenine, thymine, guanine and cytosine with respect to hybridization and primer extension in amplification reactions. In a non-limiting example, if the 5-propynyl pyrimidines propyne C and/or propyne T replace one or more C or T residues in one primer which is otherwise identical to another primer in sequence and length, the two primers will have 100% sequence identity with each other. In another non-limiting example, Inosine (I) may be used as a replacement for G or T and effectively hybridize to C, A or U (uracil). Thus, if inosine replaces one or more C, A or U residues in one primer which is otherwise identical to another primer in sequence and length, the two primers will have 100% sequence identity with each other. Other such modified or universal bases may exist which would perform in a functionally similar manner for hybridization and amplification reactions and will be understood to fall within this definition of sequence identity.

As used herein, "housekeeping gene" or "core viral gene" refers to a gene encoding a protein or RNA involved in basic functions required for survival and reproduction of a bioagent. Housekeeping genes include, but are not limited to, genes encoding RNA or proteins involved in translation, replication, recombination and repair, transcription, nucleotide metabolism, amino acid metabolism, lipid metabolism, energy generation, uptake, secretion and the like.

As used herein, the term "hybridization" or "hybridize" is used in reference to the pairing of complementary nucleic acids. Hybridization and the strength of hybridization (i.e., the strength of the association between the nucleic acids) is influenced by such factors as the degree of complementary between the nucleic acids, stringency of the conditions involved, the melting temperature ($T_m$) of the formed hybrid, and the G:C ratio within the nucleic acids. A single molecule that contains pairing of complementary nucleic acids within its structure is said to be "self-hybridized." An extensive guide to nucleic hybridization may be found in Tijssen, Laboratory Techniques in Biochemistry and Molecular Biology-Hybridization with Nucleic Acid Probes, part I, chapter 2, "Overview of principles of hybridization and the strategy of nucleic acid probe assays," Elsevier (1993), which is incorporated by reference.

As used herein, the term "primer" refers to an oligonucleotide, whether occurring naturally as in a purified restriction digest or produced synthetically, that is capable of acting as a point of initiation of synthesis when placed under conditions in which synthesis of a primer extension product that is complementary to a nucleic acid strand is induced (e.g., in the presence of nucleotides and an inducing agent such as a biocatalyst (e.g., a DNA polymerase or the like) and at a suitable temperature and pH). The primer is typically single stranded for maximum efficiency in amplification, but may alternatively be double stranded. If double stranded, the primer is generally first treated to separate its strands before being used to prepare extension products. In some embodiments, the primer is an oligodeoxyribonucleotide. The primer is sufficiently long to prime the synthesis of extension products in the presence of the inducing agent. The exact lengths of the primers will depend on many factors, including temperature, source of primer and the use of the method.

As used herein, "intelligent primers" or "primers" or "primer pairs," in some embodiments, are oligonucleotides that are designed to bind to conserved sequence regions of one or more bioagent nucleic acids to generate bioagent identifying amplicons. In some embodiments, the bound primers flank an intervening variable region between the conserved binding sequences. Upon amplification, the primer pairs yield amplicons e.g., amplification products that provide base composition variability between the two or more bioagents. The variability of the base compositions allows for the identification of one or more individual bioagents from, e.g., two or more bioagents based on the base composition distinctions. In some embodiments, the primer pairs are also configured to generate amplicons amenable to molecular mass analysis. Further, the sequences of the primer members of the primer pairs are not necessarily fully complementary to the conserved region of the reference bioagent. For example, in some embodiments, the sequences are designed to be "best fit" amongst a plurality of bioagents at these conserved binding sequences. Therefore, the primer members of the primer pairs have substantial complementarity with the conserved regions of the bioagents, including the reference bioagent.

In some embodiments of the invention, the oligonucleotide primer pairs described herein can be purified. As used herein, "purified oligonucleotide primer pair," "purified primer pair," or "purified" means an oligonucleotide primer pair that is chemically-synthesized to have a specific sequence and a specific number of linked nucleosides. This term is meant to explicitly exclude nucleotides that are generated at random to yield a mixture of several compounds of the same length each with randomly generated sequence. As used herein, the term "purified" or "to purify" refers to the removal of one or more components (e.g., contaminants) from a sample.

As used herein, the term "molecular mass" refers to the mass of a compound as determined using mass spectrometry, for example, ESI-MS. Herein, the compound is preferably a nucleic acid. In some embodiments, the nucleic acid is a double stranded nucleic acid (e.g., a double stranded DNA nucleic acid). In some embodiments, the nucleic acid is an amplicon. When the nucleic acid is double stranded the molecular mass is determined for both strands. In one embodiment, the strands may be separated before introduction into the mass spectrometer, or the strands may be separated by the mass spectrometer (for example, electrospray ionization will separate the hybridized strands). The molecular mass of each strand is measured by the mass spectrometer.

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxyl-methyl) uracil, 5-fluorouracil, 5-bromouracil, 5-carboxymethylaminomethyl-2-thiouracil, 5-carboxymethyl-aminomethyluracil, dihydrouracil, inosine, N6-isopentenyladenine, 1-methyladenine, 1-methylpseudo-uracil, 1-methylguanine, 1-methylinosine, 2,2-dimethyl-guanine, 2-methyladenine, 2-methylguanine, 3-methyl-cytosine, 5-methylcytosine, N6-methyladenine, 7-methylguanine, 5-methylaminomethyluracil, 5-methoxyamino-methyl-2-thiouracil, beta-D mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

As used herein, the term "nucleobase" is synonymous with other terms in use in the art including "nucleotide," "deoxynucleotide," "nucleotide residue," "deoxynucleotide residue," "nucleotide triphosphate (NTP)," or deoxynucleotide triphosphate (dNTP). As is used herein, a nucleobase includes natural and modified residues, as described herein.

An "oligonucleotide" refers to a nucleic acid that includes at least two nucleic acid monomer units (e.g., nucleotides), typically more than three monomer units, and more typically greater than ten monomer units. The exact size of an oligonucleotide generally depends on various factors, including the ultimate function or use of the oligonucleotide. To further illustrate, oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Typically, the nucleoside monomers are linked by phosphodiester bonds or analogs thereof, including phosphorothioate, phosphorodithioate, phosphoroselenoate, phosphorodiselenoate, phosphoroanilothioate, phosphoranilidate, phosphoramidate, and the like, including associated counterions, e.g., H$^+$, NH$_4^+$, Na$^+$, and the like, if such counterions are present. Further, oligonucleotides are typically single-stranded. Oligonucleotides are optionally prepared by any suitable method, including, but not limited to, isolation of an existing or natural sequence, DNA replication or amplification, reverse transcription, cloning and restriction digestion of appropriate sequences, or direct chemical synthesis by a method such as the phosphotriester method of Narang et al. (1979) *Meth Enzymol.* 68:90-99; the phosphodiester method of Brown et al. (1979) *Meth Enzymol.* 68:109-151; the diethylphosphoramidite method of Beaucage et al. (1981) *Tetrahedron Lett.* 22:1859-1862; the triester method of Matteucci et al. (1981) *J Am Chem Soc* 103:3185-3191; automated synthesis methods; or the solid support method of U.S. Pat. No. 4,458,066, entitled "PROCESS FOR PREPARING POLYNUCLEOTIDES," issued Jul. 3, 1984 to Caruthers et al., or other methods known to those skilled in the art. All of these references are incorporated by reference.

As used herein a "sample" refers to anything capable of being analyzed by the methods provided herein. In some embodiments, the sample comprises or is suspected to comprise one or more nucleic acids capable of analysis by the methods. In certain embodiments, for example, the samples comprise nucleic acids (e.g., DNA, RNA, cDNAs, etc.) from one or more organisms, tissues, or cells. Samples can include, for example, blood, semen, saliva, urine, feces, rectal swabs, and the like. In some embodiments, the samples are "mixture" samples, which comprise nucleic acids from more than one subject or individual. In some embodiments, the methods provided herein comprise purifying the sample or purifying the nucleic acid(s) from the sample. In some embodiments, the sample is purified nucleic acid.

A "sequence" of a biopolymer refers to the order and identity of monomer units (e.g., nucleotides, etc.) in the biopolymer. The sequence (e.g., base sequence) of a nucleic acid is typically read in the 5' to 3' direction.

As is used herein, the term "single primer pair identification" means that one or more bioagents can be identified using a single primer pair. A base composition signature for an amplicon may singly identify one or more bioagents.

As used herein, a "sub-species characteristic" is a genetic characteristic that provides the means to distinguish two members of the same bioagent species. For example, one bacterial strain may be distinguished from another bacterial strain of the same species by possessing a genetic change (e.g., for example, a nucleotide deletion, addition or substitution) in one of the viral genes, such as the RNA-dependent RNA polymerase.

As used herein, in some embodiments the term "substantial complementarity" means that a primer member of a primer pair comprises between about 70%-100%, or between about 80-100%, or between about 90-100%, or between about 95-100%, or between about 99-100% complementarity with the conserved binding sequence of a nucleic acid from a given bioagent. These ranges of complementarity and identity are inclusive of all whole or partial numbers embraced within the recited range numbers. For example, and not limitation, 75.667%, 82%, 91.2435% and 97% complementarity or sequence identity are all numbers that fall within the above recited range of 70% to 100%, therefore forming a part of this description.

A "system" in the context of analytical instrumentation refers a group of objects and/or devices that form a network for performing a desired objective.

As used herein, "triangulation identification" means the use of more than one primer pair to generate a corresponding amplicon for identification of a bioagent. The more than one primer pair can be used in individual wells or vessels or in a multiplex PCR assay. Alternatively, PCR reactions may be carried out in single wells or vessels comprising a different primer pair in each well or vessel. Following amplification the amplicons are pooled into a single well or container which is then subjected to molecular mass analysis. The combination of pooled amplicons can be chosen such that the expected ranges of molecular masses of individual amplicons are not overlapping and thus will not complicate identification of signals. Triangulation is a process of elimination, wherein a first primer pair identifies that an unknown bioagent may be one of a group of bioagents. Subsequent primer pairs are used in triangulation identification to further refine the identity of the bioagent amongst the subset of possibilities generated with the earlier primer pair. Triangulation identification is complete when the identity of the bioagent is determined. The triangulation identification process may also be used to reduce false negative and false positive signals, and enable reconstruction of the origin of hybrid or otherwise engineered bioagents. For example, identification of the three part toxin genes typical of *B. anthracis* (Bowen et al., *J Appl Microbiol*, 1999, 87, 270-278) in the absence of the expected compositions from the *B. anthracis* genome would suggest a genetic engineering event.

As used herein, the term "unknown bioagent" can mean, for example: (i) a bioagent whose existence is not known (for example, the SARS coronavirus was unknown prior to April 2003) and/or (ii) a bioagent whose existence is known (such as the well known bacterial species *Staphylococcus aureus* for example) but which is not known to be in a sample to be analyzed. For example, if the method for identification of coronaviruses disclosed in commonly owned U.S. patent Ser. No. 10/829,826 (incorporated herein by reference in its entirety) was to be employed prior to April 2003 to identify the SARS coronavirus in a clinical sample, both meanings of "unknown" bioagent are applicable since the SARS coronavirus was unknown to science prior to April, 2003 and since it was not known what bioagent (in this case a coronavirus) was present in the sample. On the other hand, if the method of U.S. patent Ser. No. 10/829,826 was to be employed subsequent to April 2003 to identify the SARS coronavirus in a clinical sample, the second meaning (ii) of "unknown" bioagent would apply because the SARS coronavirus became known to science subsequent to April 2003 because it was not known what bioagent was present in the sample.

As used herein, the term "variable region" is used to describe a region that falls between any one primer pair described herein. The region possesses distinct base compositions between at least two bioagents, such that at least one bioagent can be identified at, for example, the family, genus, species or sub-species level. The degree of variability between the at least two bioagents need only be sufficient to allow for identification using mass spectrometry analysis, as described herein.

As used herein, a "wobble base" is a variation in a codon found at the third nucleotide position of a DNA triplet. Variations in conserved regions of sequence are often found at the third nucleotide position due to redundancy in the amino acid code.

EXPERIMENTAL

Example 1

In some embodiments, oligonucleotides of the present invention are configured to identify, detect, and/or quantify target DNA in the presence of contamination non-target DNA. In some embodiments, oligonucleotides identify, detect, and/or quantify bacterial DNA in the presence of contaminating non-bacterial DNA. In some embodiments, oligonucleotides are capable of identifying, detecting, and/ or quantifying bacterial DNA in the presence of human DNA. In some embodiments, oligonucleotides are capable of identifying, detecting, and/or quantifying bacterial DNA in the presence of an overwhelming amount of contaminating DNA (e.g. human DNA). In some embodiments, a relatively small amount of bacterial DNA is identified, detected, and/or quantified in the presence of an overwhelmingly large amount of contaminating DNA (e.g. human DNA). In some embodiments, oligonucleotides identify, detect, and/or quantify target DNA (e.g. bacterial DNA) in the presence of contaminating non-target DNA (e.g. non-bacterial DNA (e.g. human DNA)), and other contaminants (e.g. biological contaminants (e.g. blood material), environmental contaminants). In some embodiments, oligonucleotides are capable of capturing (e.g. hybridizing to) bacterial DNA in a blood sample (e.g. human blood sample). In some embodiments, oligonucleotides are capable of hybridizing to bacterial DNA in a human blood sample while discriminating against human DNA (e.g. not binding to human DNA). In some embodiments, oligonucleotides are capable of hybridizing to bacterial DNA in a sample of DNA purified from human blood.

In some embodiments, oligonucleotides provide broad general bacterial identification, detection, and/or quantification. In some embodiments, oligonucleotides provide discrimination of bacterial DNA against human DNA. In some embodiments, oligonucleotides provide broad general bacterial identification, detection, and/or quantification and discrimination against human DNA binding. In some embodiments, oligonucleotides comprise capture oligonucleotides for bacterial DNA in the presence of an overwhelming amount of human DNA. In some embodiments, oligonucleotides comprise a series of capture oligonucleotides for bacterial DNA in the presence of an overwhelming amount of human DNA using a nucleic acid detection and/or quantification platform. In some embodiments, oligonucleotides comprise a series of capture oligonucleotides for bacterial DNA in the presence of an overwhelming amount of human DNA on the Boreal SCODA technology platform. In some embodiments, the present invention provides capture of bacterial DNA, without capture of human DNA (e.g. without significant capture). In some embodiments, the present invention provides capture of bacterial DNA, without capture of human DNA (e.g. without significant capture) under specified conditions (e.g. pH, ionic strength, temperature (e.g. $T_m$), etc.). In some embodiments, the target $T_m$ for oligonucleotide binding to bacterial DNA and discrimination of human DNA binding is 20° C., 25° C., 30° C., 35° C., 40° C., 45° C., 50° C., 55° C., 60° C., 65° C., 70° C., 75° C., or temperatures therein. In some embodiments, the target $T_m$ for oligonucleotide binding to bacterial DNA and discrimination of human DNA binding is about 40° C. (e.g. 40° C.). In some embodiments, the target ionic strength for binding to bacterial DNA and discrimination of human DNA binding is 1 mM salt, 2 mM salt, 5 mM salt, 10 mM salt, 20 mM salt 50 mM salt, 100 mM salt, and ionic strengths therein. In some embodiments, the target ionic strength for binding to bacterial DNA and discrimination of human DNA binding is 10 mM salt (e.g. NaCl, KCl, MgCl, NaOAc, combinations thereof, etc.). In some embodiments, the target pH for binding to bacterial DNA and discrimination of human DNA binding is pH 5.0, pH 5.5, pH 6.0, pH 6.5, pH 7.0, pH 7.5, pH 8.0, pH 8.5, pH 9.0, pH 9.5, pH 10.0, and pH's therein.

In some embodiments, oligonucleotides are between 10 and 20 nucleotides in length (e.g. 10 nt, 11 nt, 12 nt, 13 nt, 14 nt, 15 nt, 16 nt, 17 nt, 18 nt, 19 nt, or 20 nt), although both longer and shorter oligonucleotides may be used. In some embodiments, oligonucleotides are between 8 and 40 nucleotides in length. In some embodiments, oligonucleotides are between 13 and 16 nucleotides in length.

Oligonucleotides of the present invention may find use with any suitable assay, system, or method of nucleic acid quantification, detection, and/or identification. Exemplary detection methodologies include techniques that employ amplification prior to, simultaneous with, or as a part of detection, e.g., polymerase chain reaction (PCR; U.S. Pat. Nos. 4,683,195, 4,683,202, 4,800,159 and 4,965,188, each of which is herein incorporated by reference in its entirety), reverse transcription polymerase chain reaction (RT-PCR), transcription-mediated amplification (TMA; U.S. Pat. Nos. 5,480,784 and 5,399,491, each of which is herein incorporated by reference in its entirety), ligase chain reaction (LCR; Weiss, R., *Science* 254: 1292 (1991), herein incorporated by reference in its entirety), strand displacement amplification (SDA; Walker, G. et al., *Proc. Natl. Acad. Sci. USA* 89: 392-396 (1992); U.S. Pat. Nos. 5,270,184 and 5,455,166, each of which is herein incorporated by reference in its entirety), and nucleic acid sequence based amplification (NASBA; U.S. Pat. No. 5,130,238, herein incorporated by reference in its entirety). In some embodiments, detection methodologies do not require nucleic acid amplification. Exemplary detection methodologies include techniques that employ sequencing, e.g., chain terminator (Sanger) sequencing and dye terminator sequencing, as well as "next generation" sequencing techniques (Voelkerding et al., *Clinical Chem.*, 55: 641-658, 2009; MacLean et al., *Nature Rev. Microbiol.*, 7: 287-296; each herein incorporated by reference in their entirety). In some embodiments, detection methodologies do not require nucleic acid sequencing. In some embodiments, detection, identification, and/or quantification of target nucleic acids utilize one or more labeled and/or tagged oligonucleotides, e.g. fluorescently labeled, mass tagged, etc. In some embodiments, detection, identification, and/or quantification of target nucleic acids utilize one or more nucleic acid separation techniques, e.g., gel electrophoresis, immunoprecipitation, SCODA, etc. The present invention is not limited by the type of nucleic acid identification, detection, and/or quantification assay, system, or method employed.

Experiments were performed during development of embodiments of the present invention to develop oligonucleotides configured to identify, detect, and/or quantify the bacterial DNA in the presence of an overwhelming amount of contaminating human DNA. A subset of 45 sequences (See Table 1) was first extracted from an alignment of 3160 bacterial 16S rRNA sequences from published genome sequences.

TABLE 1

List of the 45 organisms present in the representative alignment of ribosomal sequences used for the design of capture oligo.

| Accesssion # | Genus, species, strain |
| --- | --- |
| NC_010611.1 | *Acinetobacter baumannii* ACICU |
| NC_007530.2 | *Bacillus anthracis* str. 'Ames Ancestor' |
| NC_004663.1 | *Bacteroides thetaiotaomicron* VPI-5482 |
| NC_005955.1 | *Bartonella quintana* str. Toulouse |
| NC_002929.2 | *Bordetella pertussis* Tohama I |
| NC_007624.1 | *Brucella melitensis* biovar Abortus 2308 chromosome II |
| NC_008060.1 | *Burkholderia cenocepacia* AU 1054 chromosome 1 |
| NC_006350.1 | *Burkholderia pseudomallei* K96243 chromosome 1 |
| NC_008787.1 | *Campylobacter jejuni* subsp. *jejuni* 81-176 |
| NC_007429.1 | *Chlamydia trachomatis* A/HAR-13 |
| NC_005043.1 | *Chlamydophila pneumoniae* TW-183 |
| NC_003030.1 | *Clostridium acetobutylicum* ATCC 824 |
| NC_009495.1 | *Clostridium botulinum* A str. ATCC 3502 |
| NC_009089.1 | *Clostridium difficile* 630 |
| NC_003366.1 | *Clostridium perfringens* str. 13 |
| NC_011527.1 | *Coxiella burnetii* CbuG_Q212 |
| NC_006831.1 | *Ehrlichia ruminantium* str. Gardel |
| NC_002695.1 | *Escherichia coli* O157:H7 str. Sakai |
| NC_009441.1 | *Flavobacterium johnsoniae* UW101 |
| NC_008601.1 | *Francisella tularensis* subsp. *novicida* U112 |
| NC_003454.1 | *Fusobacterium nucleatum* subsp. *nucleatum* ATCC 25586 |
| NC_000907.1 | *Haemophilus influenzae* Rd KW20 |
| NC_010698.2 | *Helicobacter pylori* Shi470 |
| NC_011283.1 | *Klebsiella pneumoniae* 342 |
| NC_006368.1 | *Legionella pneumophila* str. Paris |
| NC_005823.1 | *Leptospira interrogans* serovar Copenhageni str. Fiocruz L1-130 chromosome I |
| NC_003210.1 | *Listeria monocytogenes* EGD-e |
| NC_002677.1 | *Mycobacterium leprae* TN |
| NC_000962.2 | *Mycobacterium tuberculosis* H37Rv |
| NC_000912.1 | *Mycoplasma pneumoniae* M129 |
| NC_011035.1 | *Neisseria gonorrhoeae* NCCP11945 |
| NC_003116.1 | *Neisseria meningitidis* Z2491 |
| NC_002950.2 | *Porphyromonas gingivalis* W83 |
| NC_002516.2 | *Pseudomonas aeruginosa* PAO1 |
| NC_000963.1 | *Rickettsia prowazekii* str. Madrid E |
| NC_011094.1 | *Salmonella enterica* subsp. *enterica* serovar Schwarzengrund str. CVM19633 |
| NC_009632.1 | *Staphylococcus aureus* subsp. *aureus* JH1 |
| NC_004461.1 | *Staphylococcus epidermidis* ATCC 12228 |
| NC_010380.1 | *Streptococcus pneumoniae* Hungary 19A-6 |
| NC_007297.1 | *Streptococcus pyogenes* MGAS5005 |
| NC_000919.1 | *Treponema pallidum* subsp. *pallidum* str. Nichols |
| NC_011374.1 | *Ureaplasma urealyticum* serovar 10 str. ATCC 33699 |
| NC_009457.1 | *Vibrio cholerae* O395 chromosome 2 |
| NC_004088.1 | *Yersinia pestis* KIM |
| NC_001318.1 | *Borrelia burgdorferi* B31 |

The sub-alignment was used instead of the full alignment as to minimize distribution biases in sequence databases that result from the overrepresentation of species like *E. coli* or *S. aureus* and/or uneven operon multiplicity across known pathogens. The sub-alignment was completed with the addition of a base pairing mask, which was used to thread in both the nuclear and mitochondrial human sequences. Finally, a consensus sequence (75% consensus) was created using the bacterial sequences only; this consensus sequence was used to visually scout islands of local sequence conservation suitable for the design of capture oligonucleotides. The precise length and sequence of the oligonucleotides were adjusted to: (1) minimize the overall number of mismatches across the representative bacterial species; (2) avoid the presence of more than two mismatches with any bacterial sequence; (3) keep at least 4 mismatches with both the nuclear and mitochondrial DNA sequence; (4) avoid strong composition bias (e. g. avoid >70% G+C or A+T, avoid only 3 base types present); (5) avoid the potential for a short, stable hairpin loop; (6) keep a melting temperature around 40+/−1° C. (10 mM Na+). Oligonucleotides satisfying these constraints were evaluated using BLAST searches, performed using the last version (37th assembly) of the non-redundant, reference human genome of the NCBI. For reference, an alternate search was performed against the set of complete bacterial genomes (1199 genomes as of mar. 10, 2010). Blastn searches were performed without filtering using a word size of 7 and a cutoff E-value of 1000 or 10,000.

A total of 32 oligonucleotides, covering most of the length of the small subunit rRNA were subjected to the BLAST evaluation (See Table 2). BLAST searches against bacterial genomes typically yielded hundreds of full-length matches to the designed oligonucleotides; partial hits were not reported with the loose parameters required for these searches. A few oligonucleotides yielded 1 to 3 three full-length hits against the reference human genome; in contrast to the bacterial hits, these hits are non-homologous as the oligonucleotides were designed to harbor at least 4 mismatches with the corresponding regions of either the nuclear and the mitochondrial ribosomal DNA.

TABLE 2

Blast result summary. For each oligo(left), the number of blast hits within either the human genome (center columns) or the bacterial genomes (right columns) are reported. Numbers of hits are reported left to right by decreasing bit score (or increasing E-value). N/A: not applicable (the oligo is too short to yield the type of hit reported in this particular column). ND: not determined (E-value greater than the cut-off value of 1,000 used in most human searches; partial hits were not reported for bacterial searches given the already high number of full-length hits). All oligonucleotide sequences shown in the table are from the (+) strand. The top 18 oligonucleotides showing potential for the preferential capture of bacteria DNA are shown as SEQ ID NOs: 1-18.

| SEQ ID NO. | Sequence | length | Tm (° C. (10 mM Na+) | Human genome hits (reference database GrCg37) | | | | | | | |
|---|---|---|---|---|---|---|---|---|---|---|---|
| | | | score | 33.7 | 31.9 | 30.1 | 28.3 | 26.5 | 24.7 | 22.9 | 21.1 |
| | | | E-value | | 2.1 | 7.4 | 26 | 90 | 313 | 1094 | 3819 |
| | | | | | | | 15/15 | 14/14 | 13/13 | 12/12 | 11/11 |
| | | | | | | | or | or | or | or | or |
| | | | | 18/18 | 17/17 | 16/16 | 17/18 | 16/17 | 15/16 | 14/15 | 13/14 |
| 1 | CACGCCGTAAACGA | 14 | 40.5 | N/A | N/A | N/A | N/A | 0 | 0 | 9 | 86 |
| 2 | TAGCCGTACCGGAA | 14 | 38.9 | N/A | N/A | N/A | N/A | 1 | 1 | 3 | 54 |
| 3 | GCGAACGGGTGAG | 13 | 40.1 | N/A | N/A | N/A | N/A | N/A | 2 | 13 | 252 |
| 4 | ACCGGTGGCGAAG | 13 | 41.6 | N/A | N/A | N/A | N/A | 0 | 4 | 28 | 241 |
| 5 | TGTCGTCAGCTCGTA | 15 | 40.5 | N/A | N/A | N/A | 0 | 1 | 5 | 66 | 409 |
| 6 | CGGCTAACTCCGTG | 14 | 40.1 | N/A | N/A | N/A | N/A | 1 | 7 | 79 | 446 |
| 7 | TTACTGGGCGTAAAG | 15 | 36.0 | N/A | N/A | N/A | 1 | 4 | 7 | 178 | 846 |
| 8 | ACGCGAAGAACCTTAC | 16 | 40.7 | N/A | N/A | 0 | 0 | 0 | 11 | 236 | 2413 |
| 9 | CGGCTAACTACGTGC | 15 | 41.4 | N/A | N/A | N/A | 0 | 1 | 16 | 78 | 543 |
| 10 | AGTCTGCAACTCGA | 14 | 36.8 | N/A | N/A | N/A | N/A | 3 | 17 | 378 | 2360 |
| 11 | TTAAGTCCCGCAACG | 15 | 40.3 | N/A | N/A | N/A | 1 | 3 | 19 | 128 | 558 |
| 12 | CTCCTACGGGAGGC | 14 | 40.7 | N/A | N/A | N/A | N/A | 1 | 19 | 125 | 897 |
| 13 | ACGGTCCAGACTCC | 14 | 39.8 | N/A | N/A | N/A | N/A | 2 | 22 | 311 | 1802 |
| 14 | GGAATCGCTAGTAATCG | 17 | 38.8 | N/A | 0 | 0 | 0 | 3 | 25 | 157 | 1021 |
| 15 | GTGAATACGTTCCCGG | 16 | 41.3 | N/A | N/A | 0 | 0 | 7 | 29 | 153 | 1184 |
| 16 | GGTGAATACGTTCCC | 15 | 37.2 | N/A | N/A | N/A | 1 | 5 | 29 | 212 | 1360 |
| 17 | GGAGTCGAGTTGCAG | 15 | 40.6 | N/A | N/A | N/A | 0 | 3 | 30 | 180 | 809 |
| 18 | GTGTAGCGGTGAAAT | 15 | 37.1 | N/A | N/A | N/A | 1 | 4 | 31 | 295 | 1335 |
| 19 | CCGCCTGGGGAG | 12 | 40.2 | N/A | N/A | N/A | N/A | N/A | N/A | 221 | 1004 |
| 20 | GATTTACTGGGCGTAAAG | 18 | 40.1 | 0 | 0 | 0 | 4 | 19 | 142 | ND | ND |
| 21 | ACACACGTGCTACAA | 15 | 39.1 | N/A | N/A | N/A | 0 | 21 | 170 | ND | ND |
| 22 | CACACGTGCTACAATG | 16 | 40.0 | N/A | N/A | 1 | 7 | 30 | 202 | ND | ND |
| 23 | CATGATGACTTGACGTC | 17 | 39.6 | N/A | 0 | 0 | 3 | 18 | 204 | ND | ND |
| 24 | CGGATTGTAGTCTGCAA | 17 | 40.8 | N/A | 0 | 0 | 1 | 18 | 210 | ND | ND |
| 25 | CTAGTTGGTGAGGTAA | 16 | 35.0 | N/A | N/A | 1 | 7 | 30 | 228 | ND | ND |
| 26 | TAGATACCCTGGTAGTCC | 18 | 39.6 | 0 | 0 | 1 | 5 | 32 | 228 | ND | ND |
| 27 | TGAAGTTGGAATCGCTAG | 18 | 41.0 | 0 | 0 | 0 | 4 | 19 | 239 | ND | ND |
| 28 | GAATTCCAAGTGTAGCG | 17 | 39.8 | N/A | 0 | 1 | 12 | 42 | 334 | ND | ND |
| 29 | CACACTGGGACTGAG | 15 | 39.3 | N/A | N/A | N/A | 3 | 45 | 380 | ND | ND |
| 30 | AGCTAGTTGGTGAGGTAA | 18 | 40.8 | 0 | 1 | 2 | 12 | 40 | 409 | ND | ND |
| 31 | GGGAGCAAACAGGATT | 16 | 39.9 | N/A | N/A | 2 | 13 | 70 | 569 | ND | ND |
| 32 | GGAAGGTGGGGATGA | 15 | 40.0 | N/A | N/A | N/A | 27 | 85 | 627 | ND | ND |

| | Bacterial hits (1199 genomes) | | | | | |
|---|---|---|---|---|---|---|
| | 33.7 | 31.9 | 30.1 | 28.3 | 26.5 | |
| | 2.1 | 7.2 | 25 | 87 | 304 | Primer |
| SEQ ID NO. | 18/18 | 17/17 | 16/16 | 15/15 | 14/14 | overlap |
| 1 | N/A | N/A | N/A | N/A | 124 | |
| 2 | N/A | N/A | N/A | N/A | 104 | |
| 3 | N/A | N/A | N/A | N/A | N/A | |
| 4 | N/A | N/A | 112 | ND | ND | 346F |

TABLE 2-continued

Blast result summary. For each oligo(left), the number of blast hits within either the human genome (center columns) or the bacterial genomes (right columns) are reported. Numbers of hits are reported left to right by decreasing bit score (or increasing E-value). N/A: not applicable (the oligo is too short to yield the type of hit reported in this particular column). ND: not determined (E-value greater than the cut-off value of 1,000 used in most human searches; partial hits were not reported for bacterial searches given the already high number of full-length hits). All oligonucleotide sequences shown in the table are from the (+) strand. The top 18 oligonucleotides showing potential for the preferential capture of bacteria DNA are shown as SEQ ID NOs: 1-18.

| | | | | | | |
|---|---|---|---|---|---|---|
| 5 | N/A | N/A | N/A | 2 | 133 | 348R |
| 6 | N/A | N/A | N/A | N/A | 136 | |
| 7 | N/A | N/A | N/A | 138 | ND | |
| 8 | N/A | N/A | 124 | ND | ND | 348F |
| 9 | N/A | N/A | N/A | 105 | ND | |
| 10 | N/A | N/A | N/A | N/A | 137 | |
| 11 | N/A | N/A | N/A | 131 | ND | 361F |
| 12 | N/A | N/A | N/A | N/A | 119 | |
| 13 | N/A | N/A | ND | ND | 138 | |
| 14 | N/A | 128 | ND | ND | ND | |
| 15 | N/A | N/A | 121 | ND | ND | |
| 16 | N/A | N/A | N/A | 118 | ND | |
| 17 | N/A | N/A | N/A | 134 | ND | |
| 18 | N/A | N/A | N/A | 132 | ND | |
| 19 | N/A | N/A | N/A | N/A | N/A | 347R |
| 20 | 157 | ND | ND | ND | ND | |
| 21 | N/A | N/A | N/A | 128 | ND | |
| 22 | N/A | N/A | 127 | ND | ND | |
| 23 | N/A | 141 | ND | ND | ND | |
| 24 | N/A | 136 | ND | ND | ND | |
| 25 | N/A | N/A | 114 | ND | ND | |
| | | | | | | 346R/3 |
| 26 | 117 | ND | ND | ND | ND | |
| 27 | 110 | ND | ND | ND | ND | |
| 28 | N/A | 16 | 18 | 59 | ND | |
| 29 | N/A | N/A | N/A | 137 | ND | |
| 30 | 114 | ND | ND | ND | ND | |
| 31 | N/A | N/A | 105 | ND | ND | |
| 32 | N/A | N/A | N/A | 113 | ND | 361R |

Figure 8:
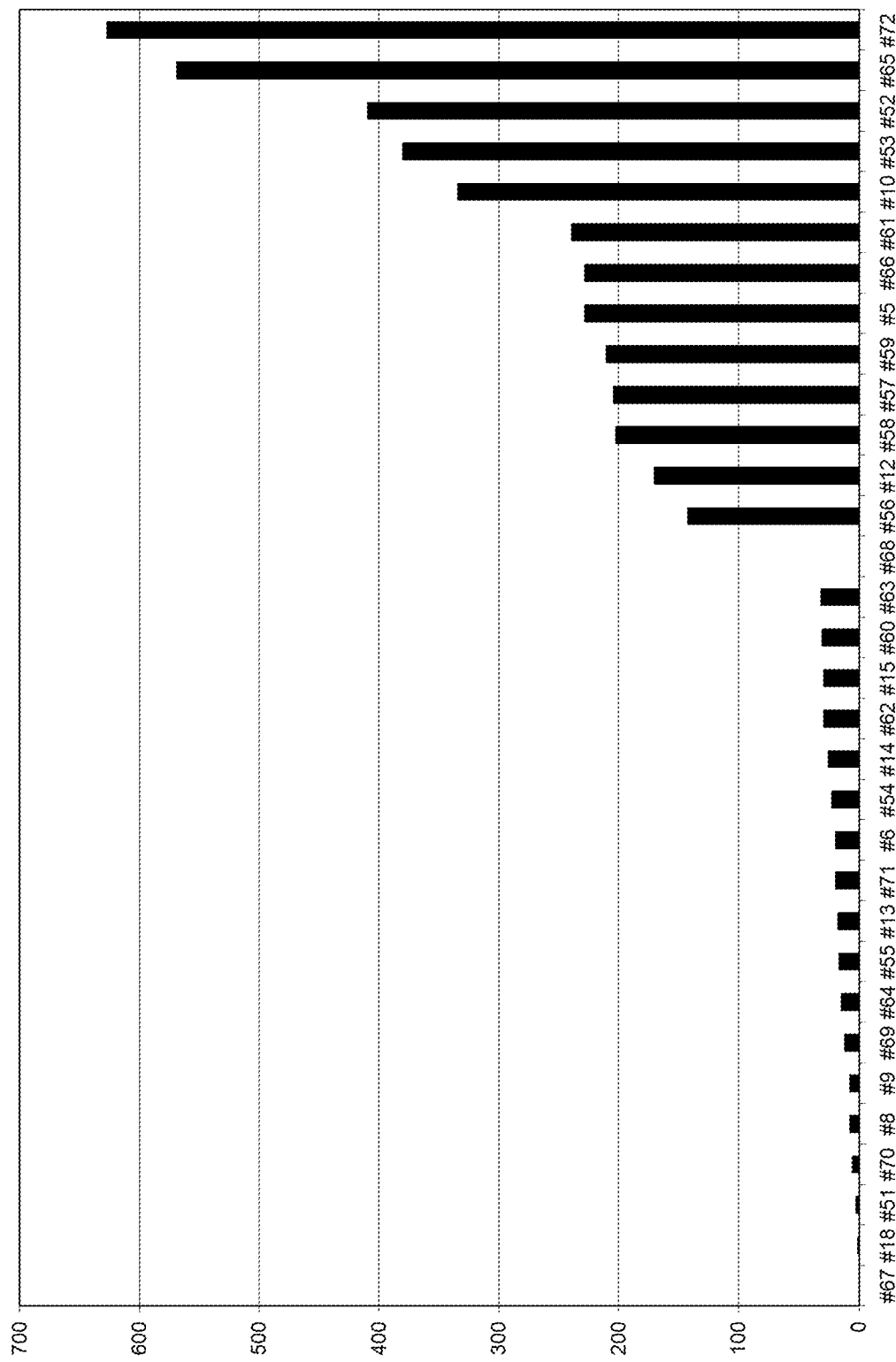
FIG. 8 shows a graph of the number of 13/13 hits or better (Evalue=313) per oligonucleotide. Oligonucleotides are designed on the x axis accordingly to their sequential number. The sequentially numbered oligonucleotides are plotted along the x-axis, and the y-axis represents the number of hits in the reference human genome with a score of 24.7 or better.

No length constraint was used during the design of the oligonucleotides; instead, oligonucleotide length was indirectly constrained by the $T_m$ requirement of 40+/1° C., which translates into most oligos being 14 to 16 nucleotides long. The oligonucleotides were classified using the number of hits scoring 24.7 or better that were produced while querying the human genome (See Table 2 and FIG. 1). This score is equivalent to having a perfect 13/13 match or better, which should also translates into a $T_m$ in the 25-30° C. range. The E-value associated with these hits is 313, meaning than 313 perfect 13-nt hits are expected to be found within the human genome. The oligos are divided in two populations (SEE FIG. 8). The top 18 show between 0 and 31 hits, i.e at least 10 times less than the number of hits expected for an oligo of random sequence. In contrast, the bottom 14 oligos show a number of hits in the same order of magnitude as the one expected. The top 18 oligonucleotides (See Table 2) are configured to identify, detect, and/or quantify bacterial DNA in the presence of contaminating human DNA, e.g., using the Boreal SCODA technology for the subsequent identification of bacterial pathogens using the Ibis platform. In particular, the top 2 oligonucleotides (See Table 2), are particularly well suited for the identification, detection, and/or quantification of bacterial DNA in the presence of contaminating human DNA.

Various modifications of the invention, in addition to those described herein, will be apparent to those skilled in the art from the foregoing description. Such modifications are also intended to fall within the scope of the appended claims. Each reference (including, but not limited to, journal articles, U.S. and non-U.S. patents, patent application publications, international patent application publications, gene bank accession numbers, internet web sites, and the like) cited in the present application is incorporated herein by reference in its entirety.

What is claimed is:

1. A kit comprising a purified oligonucleotide configured to hybridize to a broad range of bacterial genomes while discriminating against hybridizing to non-bacterial DNA wherein said purified oligonucleotide is SEQ ID NO: 1, wherein said purified oligonucleotide comprises a label, wherein said label is a fluorescent label, a luminescent label, a chemiluminescent label, a radioactive label, a quencher label, an interacting label or a mass-tagged label; and a cell lysis reagent or a cell lysis component.

2. The kit of claim 1, wherein said non-bacterial DNA comprises human genomic DNA.

3. The kit of claim 1, further comprising a gel suitable for use in SCODA purification.

4. The kit of claim 1, further comprising a component for generating an electric field, a magnetic field, a flow field or a combination thereof.

5. The kit of claim 1, wherein said purified oligonucleotide is a capture oligonucleotide immobilized in a gel suitable for SCODA purification.

6. The kit of claim 1, further comprising at least one negative control reagent.

7. The kit of claim 1, further comprising at least one PCR clean-up reagent.

8. The kit of claim 1, further comprising a capture component or molecule.

9. The kit of claim 1, further comprising an elution reagent.

10. The kit of claim 1, further comprising a detection reagent.

11. The kit of claim 1, further comprising at least one calibrant polynucleotide.

12. The kit of claim 1, further comprising a next-generation sequencing reagent or a next-generation sequencing component.

13. The kit of claim 1, further comprising a buffer component.

14. The kit of claim 1, further comprising a restriction enzyme.

15. The kit of claim 1, further comprising a nucleic acid amplification reagent or a nucleic acid amplification component.

16. The kit of claim 1, further comprising one or more purified oligonucleotides selected from SEQ ID NOs: 2-18.

17. The kit of claim 16, wherein at least one of said one or more purified oligonucleotides is a capture oligonucleotide immobilized in a gel suitable for SCODA purification.

* * * * *

SEQUENCE LISTING

<160> NUMBER OF SEQ ID NOS: 32

<210> SEQ ID NO 1
<211> LENGTH: 14
<212> TYPE: DNA
<213> ORGANISM: artificial sequence
<220> FEATURE:
<223> OTHER INFORMATION: synthetic

<400> SEQUENCE: 1

```
cacgccgtaa acga                                                  14

<210> SEQ ID NO 2
<211> LENGTH: 14
<212> TYPE: DNA
<213> ORGANISM: artificial sequence
<220> FEATURE:
<223> OTHER INFORMATION: synthetic

<400> SEQUENCE: 2
tagccgtacc ggaa                                                  14

<210> SEQ ID NO 3
<211> LENGTH: 13
<212> TYPE: DNA
<213> ORGANISM: artificial sequence
<220> FEATURE:
<223> OTHER INFORMATION: synthetic

<400> SEQUENCE: 3
gcgaacgggt gag                                                   13

<210> SEQ ID NO 4
<211> LENGTH: 13
<212> TYPE: DNA
<213> ORGANISM: artificial sequence
<220> FEATURE:
<223> OTHER INFORMATION: synthetic

<400> SEQUENCE: 4
accggtggcg aag                                                   13

<210> SEQ ID NO 5
<211> LENGTH: 15
<212> TYPE: DNA
<213> ORGANISM: artificial sequence
<220> FEATURE:
<223> OTHER INFORMATION: synthetic

<400> SEQUENCE: 5
tgtcgtcagc tcgta                                                 15

<210> SEQ ID NO 6
<211> LENGTH: 14
<212> TYPE: DNA
<213> ORGANISM: artificial sequence
<220> FEATURE:
<223> OTHER INFORMATION: synthetic

<400> SEQUENCE: 6
cggctaactc cgtg                                                  14

<210> SEQ ID NO 7
<211> LENGTH: 15
<212> TYPE: DNA
<213> ORGANISM: artificial sequence
<220> FEATURE:
<223> OTHER INFORMATION: synthetic

<400> SEQUENCE: 7
ttactgggcg taaag                                                 15

<210> SEQ ID NO 8
<211> LENGTH: 16
<212> TYPE: DNA
<213> ORGANISM: artificial sequence
```

```
<220> FEATURE:
<223> OTHER INFORMATION: synthetic

<400> SEQUENCE: 8
acgcgaagaa ccttac                                                     16

<210> SEQ ID NO 9
<211> LENGTH: 15
<212> TYPE: DNA
<213> ORGANISM: artificial sequence
<220> FEATURE:
<223> OTHER INFORMATION: synthetic

<400> SEQUENCE: 9
cggctaacta cgtgc                                                      15

<210> SEQ ID NO 10
<211> LENGTH: 14
<212> TYPE: DNA
<213> ORGANISM: artificial sequence
<220> FEATURE:
<223> OTHER INFORMATION: synthetic

<400> SEQUENCE: 10
agtctgcaac tcga                                                       14

<210> SEQ ID NO 11
<211> LENGTH: 15
<212> TYPE: DNA
<213> ORGANISM: artificial sequence
<220> FEATURE:
<223> OTHER INFORMATION: synthetic

<400> SEQUENCE: 11
ttaagtcccg caacg                                                      15

<210> SEQ ID NO 12
<211> LENGTH: 14
<212> TYPE: DNA
<213> ORGANISM: artificial sequence
<220> FEATURE:
<223> OTHER INFORMATION: synthetic

<400> SEQUENCE: 12
ctcctacggg aggc                                                       14

<210> SEQ ID NO 13
<211> LENGTH: 14
<212> TYPE: DNA
<213> ORGANISM: artificial sequence
<220> FEATURE:
<223> OTHER INFORMATION: synthetic

<400> SEQUENCE: 13
acggtccaga ctcc                                                       14

<210> SEQ ID NO 14
<211> LENGTH: 17
<212> TYPE: DNA
<213> ORGANISM: artificial sequence
<220> FEATURE:
<223> OTHER INFORMATION: synthetic

<400> SEQUENCE: 14
ggaatcgcta gtaatcg                                                    17
```

```
<210> SEQ ID NO 15
<211> LENGTH: 16
<212> TYPE: DNA
<213> ORGANISM: artificial sequence
<220> FEATURE:
<223> OTHER INFORMATION: synthetic

<400> SEQUENCE: 15
gtgaatacgt tcccgg                                                    16

<210> SEQ ID NO 16
<211> LENGTH: 15
<212> TYPE: DNA
<213> ORGANISM: artificial sequence
<220> FEATURE:
<223> OTHER INFORMATION: synthetic

<400> SEQUENCE: 16
ggtgaatacg ttccc                                                     15

<210> SEQ ID NO 17
<211> LENGTH: 15
<212> TYPE: DNA
<213> ORGANISM: artificial sequence
<220> FEATURE:
<223> OTHER INFORMATION: synthetic

<400> SEQUENCE: 17
ggagtcgagt tgcag                                                     15

<210> SEQ ID NO 18
<211> LENGTH: 15
<212> TYPE: DNA
<213> ORGANISM: artificial sequence
<220> FEATURE:
<223> OTHER INFORMATION: synthetic

<400> SEQUENCE: 18
gtgtagcggt gaaat                                                     15

<210> SEQ ID NO 19
<211> LENGTH: 12
<212> TYPE: DNA
<213> ORGANISM: artificial sequence
<220> FEATURE:
<223> OTHER INFORMATION: synthetic

<400> SEQUENCE: 19
ccgcctgggg ag                                                        12

<210> SEQ ID NO 20
<211> LENGTH: 18
<212> TYPE: DNA
<213> ORGANISM: artificial sequence
<220> FEATURE:
<223> OTHER INFORMATION: synthetic

<400> SEQUENCE: 20
gatttactgg gcgtaaag                                                  18

<210> SEQ ID NO 21
<211> LENGTH: 15
<212> TYPE: DNA
<213> ORGANISM: artificial sequence
<220> FEATURE:
<223> OTHER INFORMATION: synthetic
```

<400> SEQUENCE: 21
acacacgtgc tacaa                                                                    15

<210> SEQ ID NO 22
<211> LENGTH: 16
<212> TYPE: DNA
<213> ORGANISM: artificial sequence
<220> FEATURE:
<223> OTHER INFORMATION: synthetic

<400> SEQUENCE: 22
cacacgtgct acaatg                                                                   16

<210> SEQ ID NO 23
<211> LENGTH: 17
<212> TYPE: DNA
<213> ORGANISM: artificial sequence
<220> FEATURE:
<223> OTHER INFORMATION: synthetic

<400> SEQUENCE: 23
catgatgact tgacgtc                                                                  17

<210> SEQ ID NO 24
<211> LENGTH: 17
<212> TYPE: DNA
<213> ORGANISM: artificial sequence
<220> FEATURE:
<223> OTHER INFORMATION: synthetic

<400> SEQUENCE: 24
cggattgtag tctgcaa                                                                  17

<210> SEQ ID NO 25
<211> LENGTH: 16
<212> TYPE: DNA
<213> ORGANISM: artificial sequence
<220> FEATURE:
<223> OTHER INFORMATION: synthetic

<400> SEQUENCE: 25
ctagttggtg aggtaa                                                                   16

<210> SEQ ID NO 26
<211> LENGTH: 18
<212> TYPE: DNA
<213> ORGANISM: artificial sequence
<220> FEATURE:
<223> OTHER INFORMATION: synthetic

<400> SEQUENCE: 26
tagataccct ggtagtcc                                                                 18

<210> SEQ ID NO 27
<211> LENGTH: 18
<212> TYPE: DNA
<213> ORGANISM: artificial sequence
<220> FEATURE:
<223> OTHER INFORMATION: synthetic

<400> SEQUENCE: 27
tgaagttgga atcgctag                                                                 18

<210> SEQ ID NO 28

```
<211> LENGTH: 17
<212> TYPE: DNA
<213> ORGANISM: artificial sequence
<220> FEATURE:
<223> OTHER INFORMATION: synthetic

<400> SEQUENCE: 28
gaattccaag tgtagcg                                                    17

<210> SEQ ID NO 29
<211> LENGTH: 15
<212> TYPE: DNA
<213> ORGANISM: artificial sequence
<220> FEATURE:
<223> OTHER INFORMATION: synthetic

<400> SEQUENCE: 29
cacactggga ctgag                                                      15

<210> SEQ ID NO 30
<211> LENGTH: 18
<212> TYPE: DNA
<213> ORGANISM: artificial sequence
<220> FEATURE:
<223> OTHER INFORMATION: synthetic

<400> SEQUENCE: 30
agctagttgg tgaggtaa                                                   18

<210> SEQ ID NO 31
<211> LENGTH: 16
<212> TYPE: DNA
<213> ORGANISM: artificial sequence
<220> FEATURE:
<223> OTHER INFORMATION: synthetic

<400> SEQUENCE: 31
gggagcaaac aggatt                                                     16

<210> SEQ ID NO 32
<211> LENGTH: 15
<212> TYPE: DNA
<213> ORGANISM: artificial sequence
<220> FEATURE:
<223> OTHER INFORMATION: synthetic

<400> SEQUENCE: 32
ggaaggtggg gatga                                                      15
```